(12) United States Patent
Badami et al.

(10) Patent No.: US 7,239,397 B2
(45) Date of Patent: Jul. 3, 2007

(54) DEVICE FOR HIGH-ACCURACY MEASUREMENT OF DIMENSIONAL CHANGES

(75) Inventors: Vivek G. Badami, Pittsford, NY (US); Steven R. Patterson, Livermore, CA (US)

(73) Assignee: Corning Incorporated, Corning, NY (US)

( * ) Notice: Subject to any disclaimer, the term of this patent is extended or adjusted under 35 U.S.C. 154(b) by 367 days.

(21) Appl. No.: 10/900,484

(22) Filed: Jul. 27, 2004

(65) Prior Publication Data

US 2005/0140983 A1   Jun. 30, 2005

Related U.S. Application Data

(60) Provisional application No. 60/533,810, filed on Dec. 31, 2003.

(51) Int. Cl.
*G01B 9/02* (2006.01)

(52) U.S. Cl. .................. 356/503; 356/485; 356/492

(58) Field of Classification Search ............... 356/503, 356/498, 493, 492, 485–487, 495, 511–514
See application file for complete search history.

(56) References Cited

U.S. PATENT DOCUMENTS

| | | | | |
|---|---|---|---|---|
| 4,733,967 A | * | 3/1988 | Sommargren | 356/484 |
| 5,818,588 A | * | 10/1998 | Matsumoto et al. | 356/487 |
| 6,480,286 B1 | * | 11/2002 | Kubo et al. | 356/503 |
| 6,504,615 B1 | * | 1/2003 | Abe et al. | 356/511 |
| 6,847,458 B2 | * | 1/2005 | Freischlad et al. | 356/503 |
| 6,885,459 B2 | * | 4/2005 | Muller | 356/503 |

OTHER PUBLICATIONS

V.G. Badami and M. Linder, "Ultra-High Accuracy Measurement of the Coefficient of Thermal Expansion for Ultra-Low Expansion Materials," to appear in Proc. SPIE, vol. 4688, pp. 469-480, 2001.
Corning ULE Glass Catalog, 2001.
Hagy and Shirkey, Determining absolute thermal expansion of titania-silica glasses: a refined ultrasonic method, Appl. Opt., 14, 2099-2103 (1975).
Specification for Extreme Ultraviolet Lithography Mask Substrates, SEMI P37-1101, 2001.
M. Okaji, N. Yamada, K. Nara, H. Kato, "Laser interferometric dilatometer at low temperatures: application to fused silica SRM 739,"Cryogenics 35, pp. 887-891, 1995.
E.G. Wolff and S. A. Eselun, "Double Michelson interferometer for conactless thermal expansion measurements," Proc. SPIE, vol. 193, pp. 204-208, 1979.

(Continued)

*Primary Examiner*—Hwa (Andrew) Lee
(74) *Attorney, Agent, or Firm*—Timothy M. Schaeberle

(57) ABSTRACT

Thermal expansion characteristics of test materials of ultra-low thermal expansion material are measured with a test beam that is split into a test material-measuring portion and an instrument-measuring portion. Both measuring portions propagate through common portions of a test arm. The test material-measuring portion encounters a test material, but the instrument-measuring portion does not. Thermal expansion characteristics of the test material are measured to high accuracy by manipulating the measures to distinguish displacements associated with the test material from displacements associated with the instrument structure.

47 Claims, 14 Drawing Sheets

OTHER PUBLICATIONS

S.J. Bennett, An absolute interferometric dilatometer, „ J. Phys. E: Sci. Instrum., 10, pp. 525-530, 1977.

W. Hou and T. Thalmann, Thermal expansion measurement of gauge Block Metrology, pp. 272-278, 1998.

E. G. Wolff and R. C. Savedra, "Precision Interferometric Dilatometer," Rev. Sci. Instrum., 53 (7), pp. 1313-1319, 1985.

S.F. Jacobs, J. N. Bradford and J. W. Berthold III, "Ultraprecise Measurements of the Thermal Coefficients of Expansion," Applied Optics, 9 (11), pp. 2477-2480, 1970.

* cited by examiner

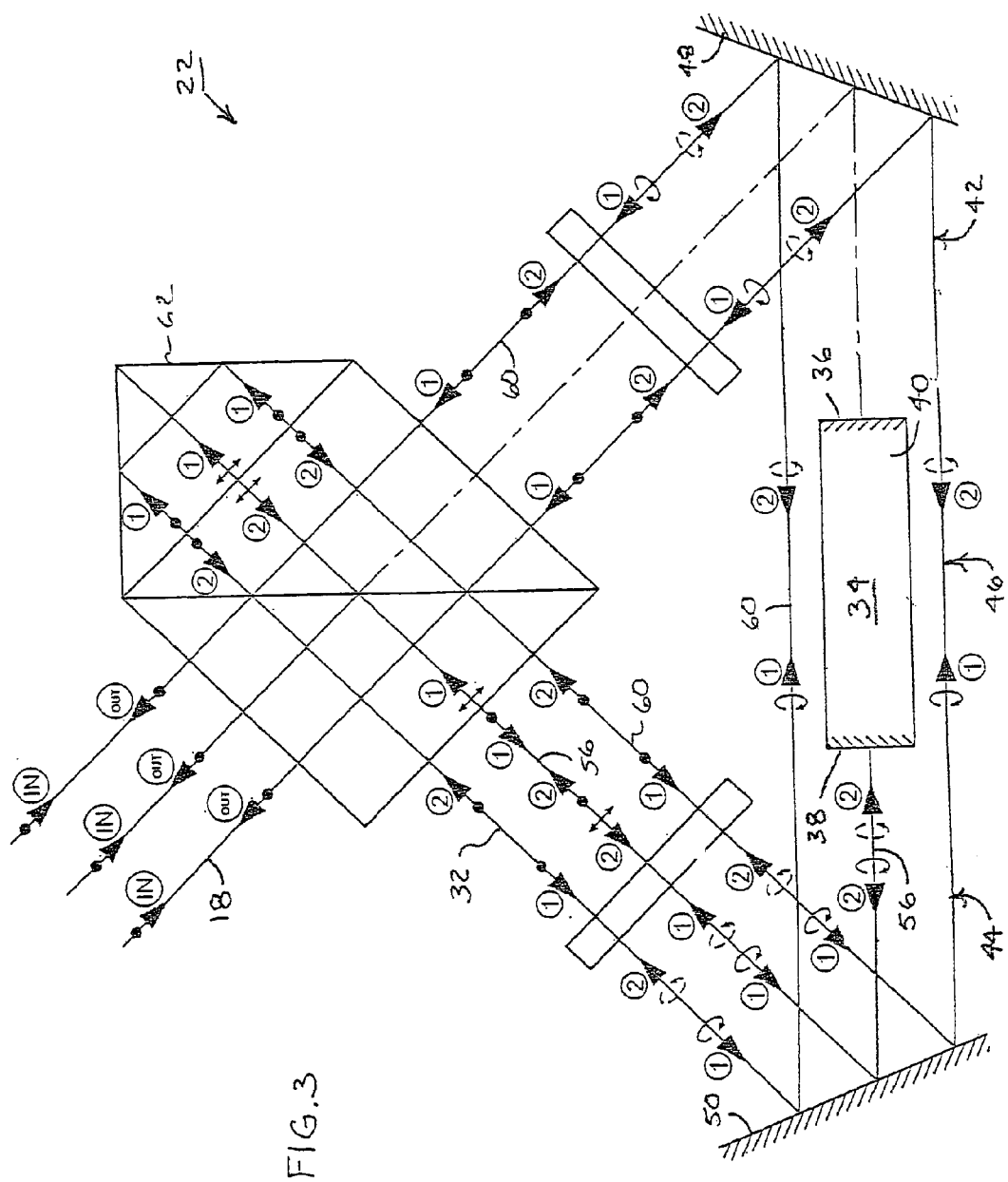

DEVICE FOR HIGH-ACCURACY MEASUREMENT OF DIMENSIONAL CHANGES

CROSS-REFERENCE TO RELATED APPLICATION

This application claims the benefit of priority under 35 U.S.C. §·119(e) of U.S. Provisional Application Ser. No. 60/533,810 filed on Dec. 31, 2003.

TECHNICAL FIELD

The invention relates to precision instruments for measuring dimensional changes of materials, particularly those applied to the measurement of thermal expansion/contraction characteristics of ultra-low thermal expansion materials.

BACKGROUND

Ultra-low thermal expansion materials such as ULE® Glass (a trademark of Corning Incorporated) and Zerodur® (a trademark of Schott Glas) provide dimensional stability for a variety of precision applications including structures requiring significant dimensional stability over a range of temperatures. Examples include structural materials for precision machines and instruments and substrates for space optics, telescopes, and extreme ultra-violet lithography (EUVL) optics and photomasks.

For such purposes as calibration, certification, and process feedback, precise measurements are required of the thermal expansion characteristics of these ultra-low expansion materials (referred to as coefficient of thermal expansion measurements or CTE measurements). However, since few if any materials exhibit lower thermal expansion characteristics, the instruments (referred to as devices) used for measuring ultra-low thermal expansion materials are often subject to nearly the same or even greater thermally induced dimensional variations. The CTE measurements are taken at different temperatures to relate dimensional changes to changes in temperature. Accompanying thermal deformations of the measuring instrument are generally the largest source of uncertainty in the CTE measurements.

Prior CTE measuring instruments (devices) that measure ultra-low thermal expansion material variations using the mechanism of interference have attempted to compensate for such instrument errors in two primary ways. Some employ common path interferometry so that machine changes equally affect the common path portions of test and reference beams. However, these interferometers have difficulty consistently relating the test and reference beams where the beams depart in the vicinity of the test materials under investigation. Joints and other connections between reference surfaces and the test material are significant sources of error. Other such instruments include a first interferometer for measuring the test material and a second interferometer for simultaneously measuring the instrument. The simultaneous measurements are generally taken along parallel paths. However, the instrument-measuring path does not account for all of the spurious variations undergone by the test material-measuring path.

SUMMARY OF THE INVENTION

Our invention is intended to increase the accuracy of dimensional change measurements, such as CTE (coefficient of thermal expansion) measurements of ultra-low thermal expansion materials by better estimating and compensating for instrument and sample errors. Dimensional changes of measuring instruments that contribute to the uncertainty of measured dimensional changes of materials are themselves accurately measured and subtracted from the measured dimensional changes of the materials. With the exception of reflections from end surfaces of the measured materials, which can be accommodated in other ways, the entire measurement path of the instrument is preferably measured to better distinguish the dimensional changes of the measured materials from dimensional changes of the measuring instrument.

A preferred configuration of our new measuring instrument readily accommodates measurements of different length test materials such as ultra-low thermal expansion materials. Auxiliary optics forming joints or connections with the end surfaces or other parts of the test materials are preferably eliminated to reduce sources of error, provide increased design flexibility, and simplify a comparison between measurements of the materials and self-measurements of the new instrument. The preferred configuration is also readily adaptable to alternative configurations for making comparisons with conventional measuring protocols.

An exemplary device for measuring dimensional changes of a test material in accordance with our invention includes the usual features of a source for producing a measuring beam, a main beam router that divides the measuring beam into test and reference beams, and a measuring loop that includes an optical pathway to the test material. However, our invention also includes a test beam router that directs both a test material-measuring portion of the test beam and an instrument-measuring portion of the test beam along a common path of the measuring loop that includes the optical pathway to the test material. The test material-measuring portion of the test beam acquires information concerning length variations of the test material in combination with length variations of the measuring loop. The instrument-measuring portion of the test beam acquires information concerning length variations of the measuring loop independently of the length variations of the test material.

The main beam router recombines the test material-measuring portion of the test beam with a first portion of the reference beam and recombines the instrument-measuring portion of the test beam with a second portion of the reference beam. Optical path length differences between the recombined test and reference beams are converted by a data acquisition system into processable measures relating to displacements of the test material and the measuring loop. A data processor manipulates the displacement measurements to separate the length variations of the measuring loop from the length variations of the test material to produce a measure of the length variation of the test material.

The device can be specially arranged as a dilatometer for measuring a thermal expansion/contraction characteristic of the test material. For this purpose, a temperature modifying system is used to produce a temperature variation in the test material along with a measurement of the temperature variation. The data acquisition system associates the manipulated displacement measurements with the measurement of temperature variation to produce the measure of the length variation of the test material in relation to the temperature variation of the test material.

The measuring loop preferably includes a first loop portion that joins a first end surface of the test material to the test beam router, a second loop portion that joins a second end surface of the test material to the test beam router, and a third loop portion that joins the first and second loop portions between the first and second end surfaces of the test material. The first loop portion preferably conveys a first test material-measuring portion of the test beam in opposite directions between the test beam router and a first end surface of the test material, and the second loop portion preferably conveys a second test material-measuring portion of the test beam in opposite directions between the test beam router and a second end surface of the test material. In addition, the first, second, and third loop portions preferably convey the instrument-measuring portion of the test beam along the measuring loop beginning and ending at the test beam router.

In a preferred device configuration, the displacement measurements are extracted from heterodyne measurement signals. A multi-frequency laser source produces a beam of light having two primary frequencies. A main beam router initially provides for dividing the two-frequency beam into a two-frequency test beam and a two-frequency reference beam. A test arm that receives the two-frequency test beam includes a test beam router that divides the two-frequency test beam into a first-frequency test beam and a second-frequency test beam. A measuring loop within the test arm includes (a) a first loop portion that joins a first end surface of the test material to the test beam router, (b) a second loop portion that joins a second end surface of the test material to the test beam router, and (c) a third loop portion that joins the first and second loop portions between the first and second end surfaces of the test material.

A test material-measuring portion of the first-frequency test beam propagates along the first loop portion reflecting from the first end surface of the test material. An instrument-measuring portion of the first-frequency test beam propagates respectively along the first, third, and second loop portions past (e.g., through an opening or around) the test material on a nominally circular route beginning and ending at the test beam router. A test material-measuring portion of the second-frequency test beam propagates along the second loop portion reflecting from the second end surface of the test material. An instrument-measuring portion of the second-frequency test beam propagates respectively along the second, third, and first loop portions past (e.g., through an opening or around) the test material on a nominally circular route beginning and ending at the test beam router. All four measuring portions of the test beam are returned to the main beam router.

A reference arm, which can include a retro-reflective optic, returns first- and second-frequency portions of the two-frequency reference beam to the main router. The two-frequency test and reference beams are recombined by the main beam router and directed to a data acquisition system that separates the combined beams into four heterodyne signals as follows:

The test material-measuring portion of the first-frequency test beam is combined with a first portion of the second-frequency reference beam to form a first heterodyne signal.

The test material-measuring portion of the second-frequency test beam is combined with a first portion of the first-frequency reference beam to form a second heterodyne signal.

The instrument-measuring portion of the first-frequency test beam is combined with a second portion of the second-frequency reference beam to form a third heterodyne signal.

The instrument-measuring portion of the second-frequency test beam is combined with a second portion of the first-frequency reference beam to form a fourth heterodyne signal.

The data acquisition system converts the four heterodyne signals into displacement-measuring signals. Conventional electronic processing synchronously demodulates the four heterodyne signals against a common beat frequency reference signal, each of which averages phase differences across beam width. Phase shifts between the reference signal and each of the heterodyne signals are interpreted as displacement measurements.

A data processor receives the four displacement-measuring signals from the data acquisition system. The four displacement-measuring signals are manipulated with each other for separating errors due to length variations of the measuring loop from length variations of the test material to provide a measure of the length variation of the test material.

For measuring a thermal expansion/contraction characteristic of the test material, such as an ultra-low thermal expansion material, a temperature modifying system is added to vary the temperature of the test material during the measurement and to produce a temperature variation-measuring signal indicative of the variation in the temperature of the test material. The data processor receives the temperature variation-measuring signal from the temperature modifying system and associates four displacement-measuring signals with the temperature variation-measuring signal to provide the measure of the length variation of the test material with respect to the temperature variation of the test material.

The two frequencies emitted by the multi-frequency laser source are preferably linearly polarized in different orthogonal directions. The test beam router is preferably a polarizing beamsplitter that exploits the different linear polarizations to separate the two-frequency test beam into the first-frequency test beam and the second-frequency test beam. Following a relative rotation of polarizations between the two-frequency test beam and the two-frequency reference beam, the first-frequency portions of the test beam are combined with corresponding second-frequency portions of the reference beam, and the second-frequency portions of the test beam are combined with corresponding first-frequency portions of the reference beam for forming the four heterodyne signals.

A retroreflector along with quarter-wave retarders straddling the test material can be used together with the polarizing beamsplitter to double the path lengths of the test beam portions traversing the test arm. The test material-measuring portions of the test beam reflect twice from the end surfaces of the test material, effectively doubling the measurement resolution. The quarter-wave retarders orthogonally rotate polarization during each pass (two encounters) of the test material-measuring portions of the test beam so that upon a first return, the polarizing beamsplitter directs the test material-measuring portions of the test beam to the retroreflector and upon a second return, the polarizing beamsplitter returns the test material-measuring portions to the main beam router.

The instrument-measuring portions of the test beam traverse the measuring loop twice, in opposite directions. Polarization effects of the quarter-wave retarders cancel each other; and upon retroreflection, the instrument-measuring portions of the test beam retrace their paths to the main beam router. In addition to doubling the path lengths of the test-material- and instrument-measuring portions of the test beam, the retroreflector inverts the beams. The inversion reduces sensitivity of the measurements to angular mounting variations and angular motions of the test material end surfaces and components of the measuring loop. Such odd-order differences, which can be sources of error, tend to cancel between passes.

The measuring loop of the test arm preferably has a triangular configuration with the polarizing beamsplitter located at an apex and two directional mirrors located at base vertices. The quarter-wave retarders are preferably located between the directional mirrors and the end surfaces of the test material so that the mirrors reflect linearly polarized light at non-normal incidence and the end surfaces reflect circularly polarized light at normal incidence.

It is the test material itself that preferably divides the first- and second-frequency test beams into test material-measuring and instrument-measuring portions. The test material is preferably cylindrical or the like having sides parallel with the direction of propagation between the directional mirrors and end surfaces normal to the same propagation direction. The first- and second-frequency test beams occupy more area than the end surfaces of the test material. Transverse portions of the first- and second-frequency test beams that reflect from the end surfaces constitute the test material-measuring portions of the test beams, and transverse portions of the first- and second-frequency test beams that pass by (i.e., do not reflect from) the end surfaces constitute the instrument-measuring portions of the test beams. For example, the first- and second-frequency test beams can be sized larger in diameter than the end surfaces, allowing the instrument-measuring portions of the test beams to propagate around the test material; or the test material can be formed with a hollow core, allowing the instrument-measuring portions of the test beams to propagate through the test material.

The instrument-measuring portions of the test beam contain information about the optical paths (i.e., the first and second optical loop portions) taken by the test material-measuring portions of the test beam, but also contain additional information about the optical path (i.e., the third optical loop portion) between the test material end surfaces. The additional displacement undergone by the third optical loop portion is not relevant to the displacement measurements of test material end surfaces. Preferably, any variations in the third optical loop are minimized, such as by arranging the third optical portion as vacuum space.

Not measured by the instrument-measuring portions of the test beam are changes in phase change associated with reflections from the end surfaces of the test material. However, this source of systematic error can be estimated by measuring identical test materials having different lengths. The different estimates of the coefficient of thermal expansion (CTE) can be used to estimate the systematic error.

The overall configuration of our preferred device is readily adaptable to a variety of other measuring protocols. The alternative setups of the other measuring protocols use different portions of the optical pathways of our preferred device. Some attach reference structures to the test material, which requires the test arm to accommodate both test and reference beams.

DRAWINGS

FIG. 3 is a similar diagram of the test arm showing the propagation of a second-frequency test beam also spit into a test material-measuring portion and an instrument-measuring portion.

DETAILED DESCRIPTION

Figure 1:
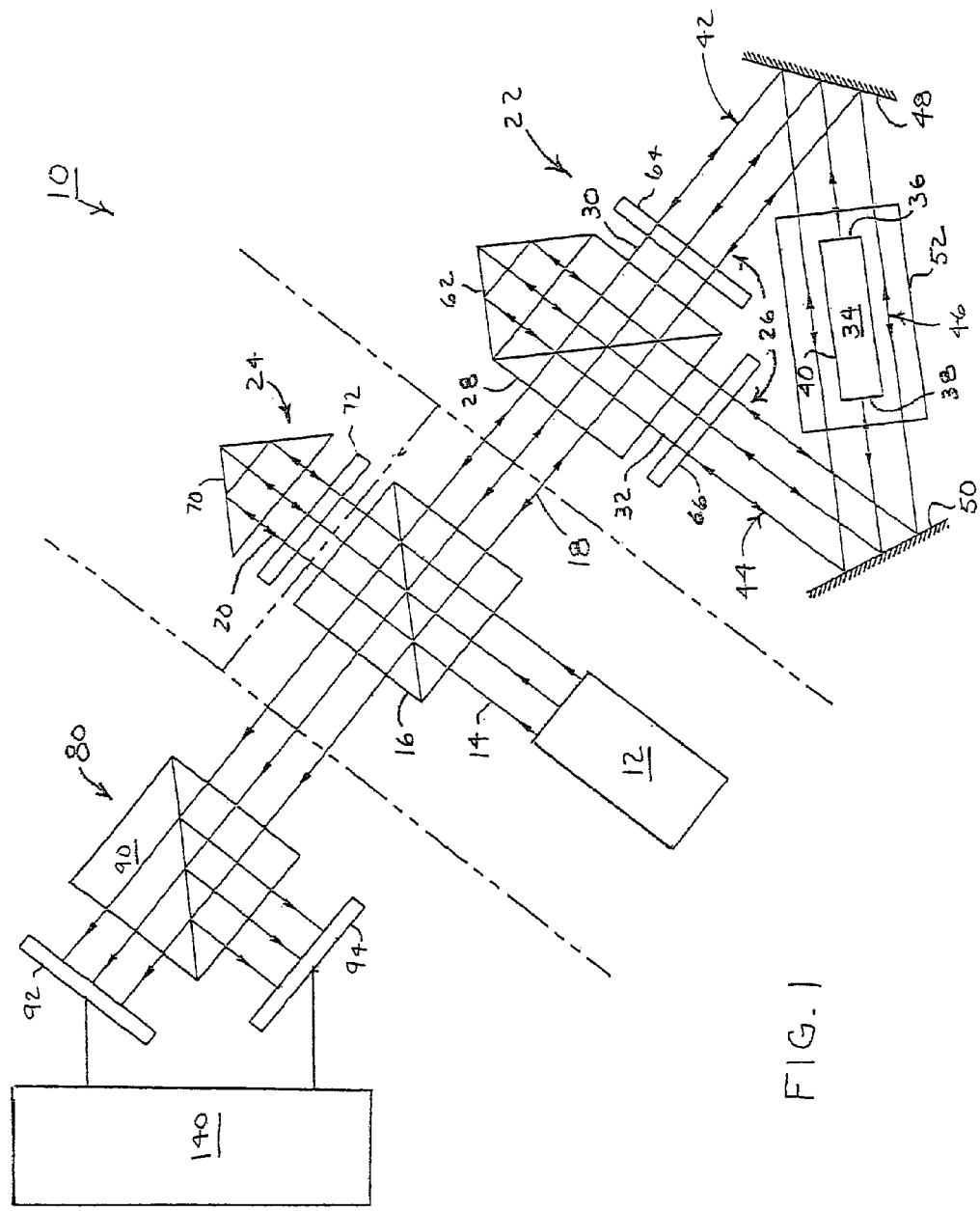
FIG. 1 is a diagram showing the layout of our preferred device.

An exemplary device 10 laid out in FIG. 1 has the general configuration of a Michelson interferometer but is specially arranged for making heterodyne displacement measurements of ultra-low thermal expansion materials. Such materials generally exhibit thermal expansions of less than 30 parts per billion per degree centigrade.

A multi-frequency laser source 12 emits an expanded beam of light 14 having two primary frequencies ($f_1$ and $f_2$) that are linearly polarized in nominally orthogonal states (p and s). The laser is preferably a HeNe laser, such as a 7712 Laserhead from Zygo Corporation, emitting two primary frequencies ($f_1$ and $f_2$), which together exhibit a beat frequency of approximately 20 megahertz. Higher or lower beat frequencies can be used, since the expected rates of change intended for measurement are slow. The cost of electronic monitoring tends to decrease with lowered beat frequencies. The measurement resolution is set by the average of the two frequencies ($f_1$ and $f_2$)

A main beam router 16, which is preferably a 50 percent partially reflective beamsplitter, divides the two-frequency beam of light into a two-frequency ($f_1$ and $f_2$) test beam 18 and a two-frequency ($f_1$ and $f_2$) reference beam 20. The two-frequency ($f_1$ and $f_2$) test beam propagates on a round trip through a test arm 22, and the two-frequency ($f_1$ and $f_2$) reference beam propagates on a round trip through a reference arm 24.

Figure 2:
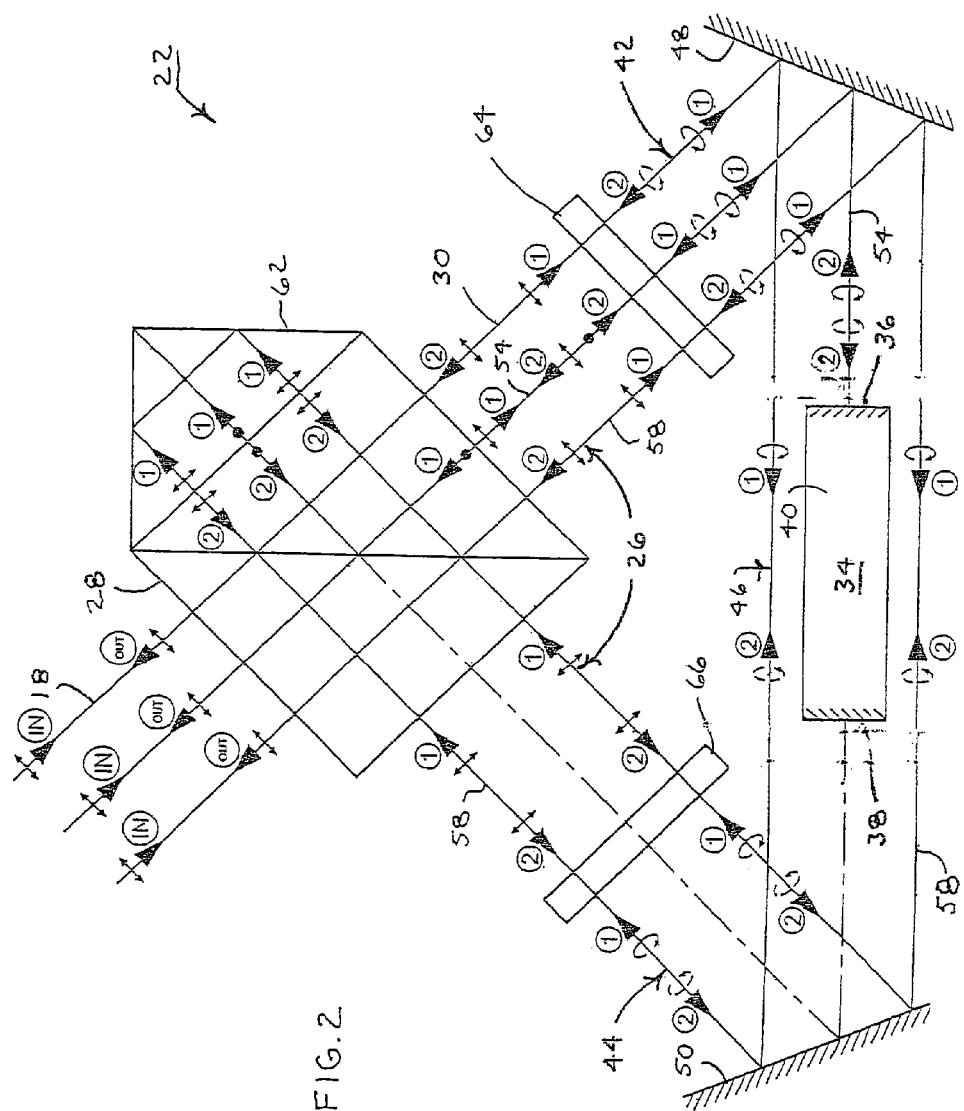
FIG. 2 is a diagram of a test arm within the device showing the propagation of a first-frequency test beam spit into a test material-measuring portion and an instrument-measuring portion.

Within the test arm 22, also shown in FIGS. 2 and 3, is a measuring loop 26 that includes test beam router 28 in the form a polarizing beamsplitter that divides the two-frequency ($f_1$ and $f_2$) test beam 18 according to its different polarization states (p and s) into a first-frequency ($f_1$) test beam 30 and a second-frequency ($f_2$) test beam 32. Also within the test arm 22 is a test material 34 made of an ultra-low thermal expansion material. The test material 34 has two plane-parallel end surfaces 36 and 38 and a body 40 having a rectangular cross section. Examples of such test material shapes are cylinders or rectangular parallelepipeds. The end surfaces 36 and 38 are polished or coated to enhance reflectivity. High reflectance metallic or dielectric coatings are contemplated for this.

The measuring loop 26 includes a first loop portion 42 that joins the test material end surface 36 to the test beam router 28, a second loop portion 44 that joins the test material end surface 38 to the test beam router 28, and a third loop portion 46 that joins the first and second loop portions 42 and 44 between the two end surfaces 36 and 38 of the test material 34. A directional mirror 48 located along the first loop portion 42 aligns the first-frequency ($f_1$) test beam 30 normal to the test material end surface 36, and a directional mirror 50 located along the second loop portion 44 aligns the second-frequency ($f_2$) test beam 32 normal to the test material end surface 38. Thus, the measuring loop 26 has an overall triangular configuration with the test beam router 28 located at an apex and the two directional mirrors 48 and 50 located at base vertices.

Both the first- and the second-frequency ($f_1$ and $f_2$) test beams 30 and 32 have transverse areas that are larger than areas occupied by the test material end surfaces 36 and 38. In the example shown, the test beams 30 and 32 have larger diameters than the end surfaces 36 and 38. However, a hollow space could be formed through the test material 34 to provide a similar area differential. Transverse areas of the first- and second-frequency ($f_1$ and $f_2$) test beams 30 and 32 that reflect from the end surfaces 36 and 38 constitute test material-measuring portions 54 and 56 of the test beams 30 and 32. Transverse areas of the first- and second-frequency ($f_1$ and $f_2$) test beams 30 and 32 that propagate around or through the end surfaces 36 and 38 constitute instrument-measuring portions 58 and 60 of the test beams 30 and 32.

The first loop portion 42 conveys the test material-measuring portion 54 of the first-frequency ($f_1$) test beam 30 having an initial polarization referenced as "p" in opposite directions between the test beam router 28 and the test material end surface 36. The second loop portion 44 conveys the test material-measuring portion 56 of the second-frequency ($f_2$) test beam 32 having an initial polarization referenced as "s" in opposite directions between the test beam router 28 and test material end surface 38. The third loop portion 46 that together with the first and second loop portions 42 and 44 conveys the instrument-measuring portions 58 and 60 of the first- and second-frequency ($f_1$ and $f_2$) test beams 30 and 32 having corresponding polarizations "p" and "s" in opposite directions along the measuring loop 26 beginning and ending at the test beam router 28.

Locating the test material 34 along a linear portion of the measuring loop 26 between the directional mirrors 48 and 50 allows the test arm 22 to accommodate different length test materials. No auxiliary optics are required to contact or otherwise reference the test material location. Accordingly, different length test materials taken from a common material stock can be measured and compared with each other to assess systematic errors associated with the measurement of the test material end surfaces 36 and 38.

A retroreflector 62 coupled to the test beam router 28 together with a pair of quarter-wave retarders 64 and 66 in the form of waveplates doubles path lengths of both the test material-measuring portions 54 and 56 and the instrument-measuring portions 58 and 60 of the two-frequency ($f_1$ and $f_2$) test beam 18. Upon a first pass (designated as "①") to and from the test material end surfaces 36 and 38, two encounters with the quarter-wave retarders 64 and 66 rotate the respective polarizations of the test material-measuring portions 54 and 56 of the first- and second-frequency ($f_1$ and $f_2$) test beams 30 and 32 through 90 degrees (e.g., from "p" and "s" to "s" and "p"). The test beam router 20, which is itself a polarizing beamsplitter, directs the polarization rotated test material-measuring portions 54 and 56 to the retroreflector 62, where the beam portions 54 and 56 are inverted and redirected for a second pass (designated as "②") to and from the test material end surfaces 36 and 38. The second two encounters with the quarter-wave retarders 64 and 66 restore the test material-measuring portions 54 and 56 to their original polarizations (e.g., from "s" and "p" to "p" and "s"). After completing two passes, the test material-measuring portions 54 and 56 are directed through the test beam router 28 on a return path to the main beam router 16.

The quarter-wave retarders 64 and 66 preferably impart equal but opposite directions of polarization rotation so that a pass through both as experienced by the instrument-measuring portions 58 and 60 of the first- and second-frequency ($f_1$ and $f_2$) test beams 30 and 32 has no net effect on their polarizations. However, since both instrument-measuring portions 58 and 60 return to the test beam router 28 after a first pass (designated as "①") at 90 degree rotated positions, both are directed to the retroreflector 62, where they are inverted and redirected for a second pass (designated as "②") in opposite directions along their original paths past the test material 34. After completing two passes, the instrument-measuring portions 58 and 60 are directed through the test beam router 28 on a return path to the main beam router 16.

The two passes supported by the retroreflector 62 and the quarter-wave retarders 64 and 66 effectively double the resolution of the measurements taken by both the test material-measuring portions 54 and 56 and the instrument-measuring portions 58 and 60 of the first- and second-frequency ($f_1$ and $f_2$) test beams 30 and 32. The test material-measuring portions 54 and 56 are sensitive to length variations of both the test material 34 and the first and second loop portions 42 and 44. The instrument-measuring portions 58 and 60 are sensitive to length variations of the entire measuring loop 26, which includes the first, second, and third loop portions 42, 44, and 46. The loop portion 46 preferably traverses evacuated space to have a minimal effect on the length variation of the measuring loop 26.

Between passes, the retroreflector inverts the first- and second-frequency ($f_1$ and $f_2$) test beams 30 and 32, effectively canceling the effects of odd-order errors across the beams. For example, gross rotation of the vertex mirrors 48 and 50 results in beam shear between the test and reference beams 18 and 20 rather than an angular misalignment, thus easing alignment requirements. Similarly, gross rotation of the test material 34 results in beam shear between the test and reference beams 18 and 20 rather than an angular misalignment, thus simplifying the alignment of the test material 34 and reducing the sensitivity to angular motions of the test material 34 during a measurement. Non-parallelism of the two test material end surfaces 36 and 38 also manifests itself as different amounts of beam shear between the test and reference beams 18 and 20.

Thus, the test material end surfaces 36 and 38 do not need to be exceptionally parallel from a manufacturing and alignment standpoint. The requirement for parallelism is set by the desired rejection of the contribution due to test material translation in a direction perpendicular to the axis of the test material 36. The test arm 22 can also be used to monitor the parallelism of the test material end surfaces 36 and 38 during a measurement by intercepting and analyzing the test material-measuring portions 54 and 56 before they impinge on the retroreflector 62. Excessive non-parallelism between test material surfaces results in an excessive number of fringes by this measurement.

Although depicted as being located between the test beam router 28 and each of the directional mirrors 48 and 50, the quarter-wave retarders 64 and 66 are preferably located between the directional mirrors 48 and 50 and the test material end surfaces 36 and 38. In the preferred positions, the directional mirrors 48 and 50 would be presented with linearly polarized light, which is preferable for making non-normal incidence reflections, and the test material end surfaces 36 and 38 would be presented with circularly polarized light, which has little effect on normal incidence reflections.

The test material is preferably mounted within and monitored by a temperature modifying system 52 including a radiant heat source (not shown) and an array of thermisters (also not shown) for monitoring temperature variations of the test material 34. Preferably, the temperature modifying system 52 provides for varying the temperature of the test material throughout a range between 0 degrees centigrade and 100 degrees centigrade. The temperature modifying system 52 also preferably produces a temperature-variation measuring signal corresponding to the temperature variation induced in the test material 34.

Figure 4B:
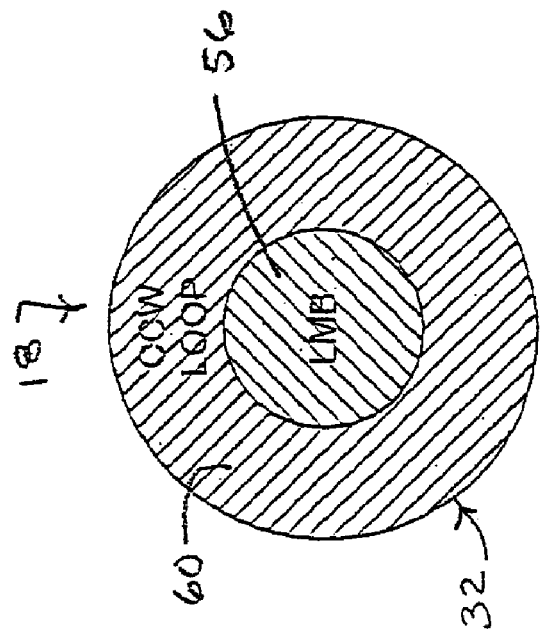
FIGS. 4A and 4B are identical cross sections of each of the first- and second-frequency test beams with the test material-measuring portions forming a central core and the instrument-measuring portions forming an outer annulus.
Figure 4A:
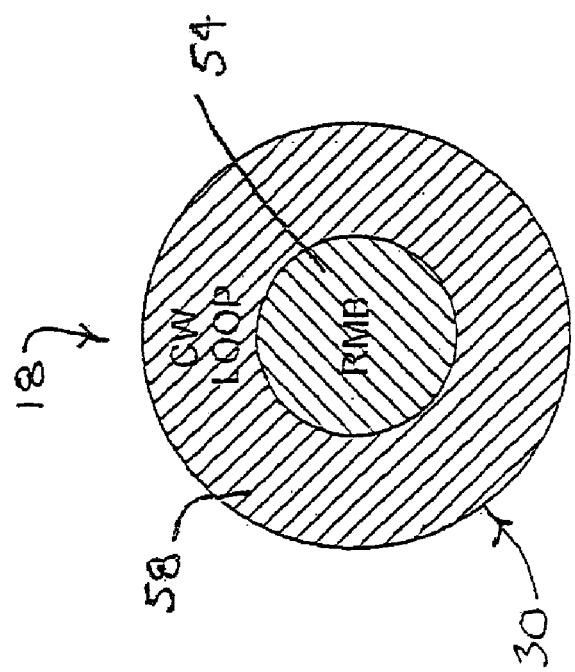

The test beam 18 returns from the test arm 22 to the main beam router 16 as a combination of two test material-measuring portions 54 and 56 and two instrument-measuring portions 58 and 60. As shown in FIGS. 4A and 4B, the two test material-measuring portions 54 and 56 occupy a common central core of the test beam 18 but are distinguished from each other in both frequency ($f_1$ or $f_2$) and polarization state (p or s). The two instrument-measuring portions 58 and 60 occupy a common outer annulus of the test beam 18 but are also distinguished from each other in both frequency ($f_1$ or $f_2$) and polarization state (p or s). The two test material-measuring portions 54 and 56 within the central core of the beam 18 encode information concerning length variations (i.e., dimensional changes) of both the test material 34 and the measuring loop 26, and the two instrument-measuring portions 58 and 60 within the common outer annulus of the test beam 18 encode information concerning length variations of the measuring loop 26 independently of the test material 34.

Figure 5:
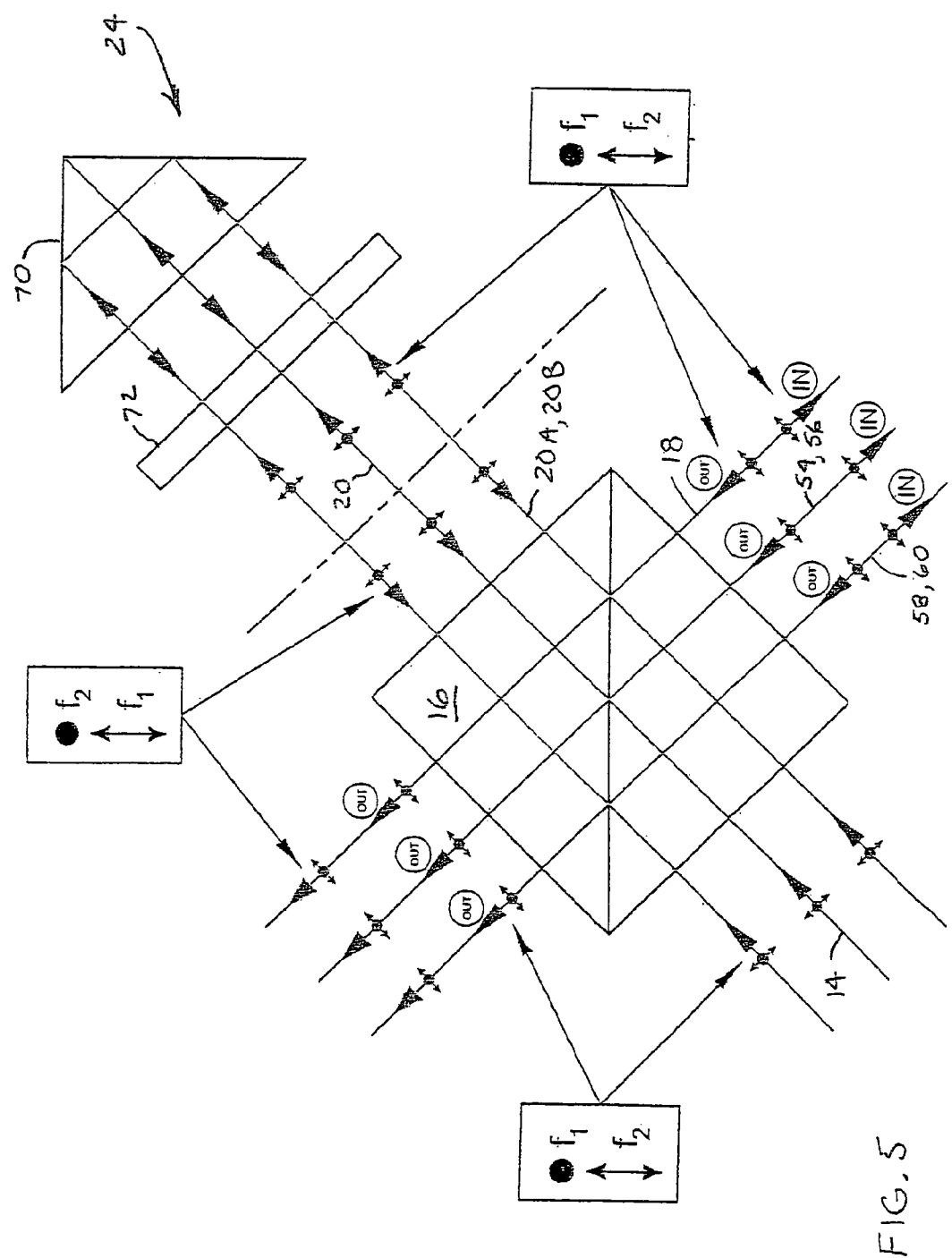
FIG. 5 is a diagram of a main beam router and a reference arm showing the routing of the two-frequency test and reference beams.

The reference arm 24 as best seen in FIG. 5 includes a retroreflector 70 and a quarter-wave retarder 72 in the form of a waveplate. The two-frequency reference beam 20, which enters the reference arm 24 as a combination of a first-frequency ($f_1$) reference beam 20A having a polarization state "p" and a second-frequency ($f_2$) reference beam 20B having a polarization state "s". However, upon encountering the quarter-wave retarder 72 twice en route to and from the retroreflector 70, the two-frequency reference beam 20 returns to the main beam router 16 with its polarizations reversed.

Having regard to both spatial position (central core or outer annulus) and polarization state (p or s), the main beam router 16 recombines the two-frequency ($f_1$ and $f_2$) test beam 18 with the two-frequency ($f_1$ and $f_2$) reference beam 20 to produce four heterodyne signal beams 82, 84, 86, and 88 (see FIG. 6) each composed of complementary frequencies ($f_1$ and $f_2$). The heterodyne signal beam 82 combines the test material-measuring portion 54 of the first-frequency ($f_1$) test beam 30 having a polarization "p" with an overlapping portion of the second-frequency ($f_2$) reference beam 20B having a matching polarization "p". The heterodyne signal beam 84 combines the test material-measuring portion 56 of the second-frequency ($f_2$) test beam 32 having a polarization "s" with an overlapping portion of the first-frequency ($f_1$) reference beam 20A having a matching polarization "s". The heterodyne signal beam 86 combines the instrument-measuring portion 58 of the first-frequency ($f_1$) test beam 30 having a polarization "p" with an overlapping portion of the second-frequency ($f_2$) reference beam 20B having a matching polarization "p". The heterodyne signal beam 88 combines the instrument-measuring portion 60 of the second-frequency ($f_2$) test beam 32 having a polarization "s" with an overlapping portion of the first-frequency ($f_1$) reference beam 20A having a matching polarization "s".

Figure 6:
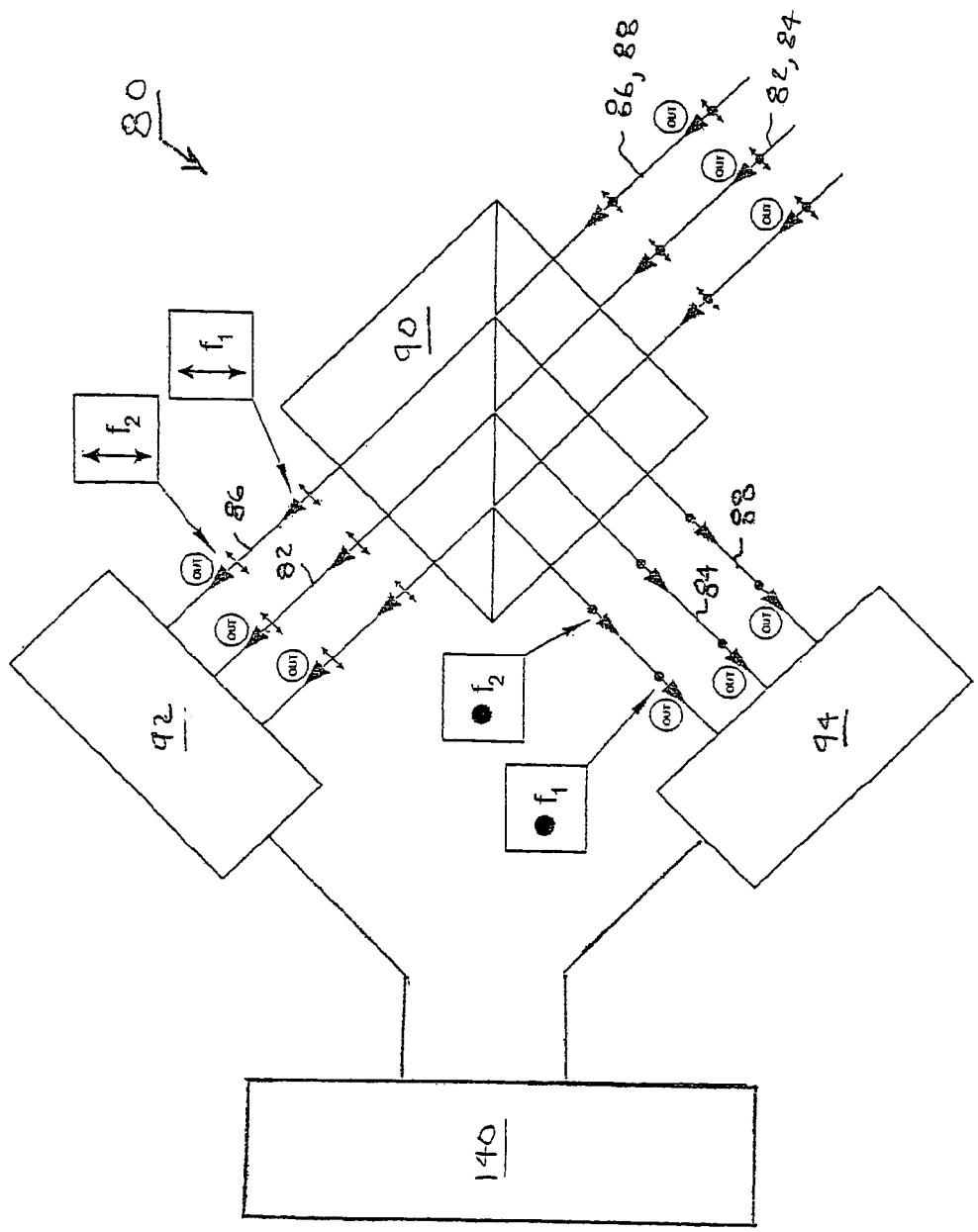
FIG. 6 is a diagram of a data acquisition system for sorting and detecting heterodyne signals from the main beam router.

A data acquisition system 80 depicted in FIG. 6 separates the four heterodyne signal beams 82, 84, 86, and 88 by polarization and spatial position and converts the heterodyne signal beams 82, 84, 86, and 88 into displacement measurements of the test material 34 and the measuring loop 26. A polarizing beamsplitter 90 directs the heterodyne signal beams 82 and 86 having a common polarization "p" to a detector module 92 and directs the heterodyne signal beams 84 and 88 having a common polarization "s" to a similar detector module 94. Within the two detector modules 92 and 94, the remaining pairings of heterodyne signal beams 82 and 86 or 84 and 88 are separated by spatial position (center portion or outer annulus).

Figure 7:
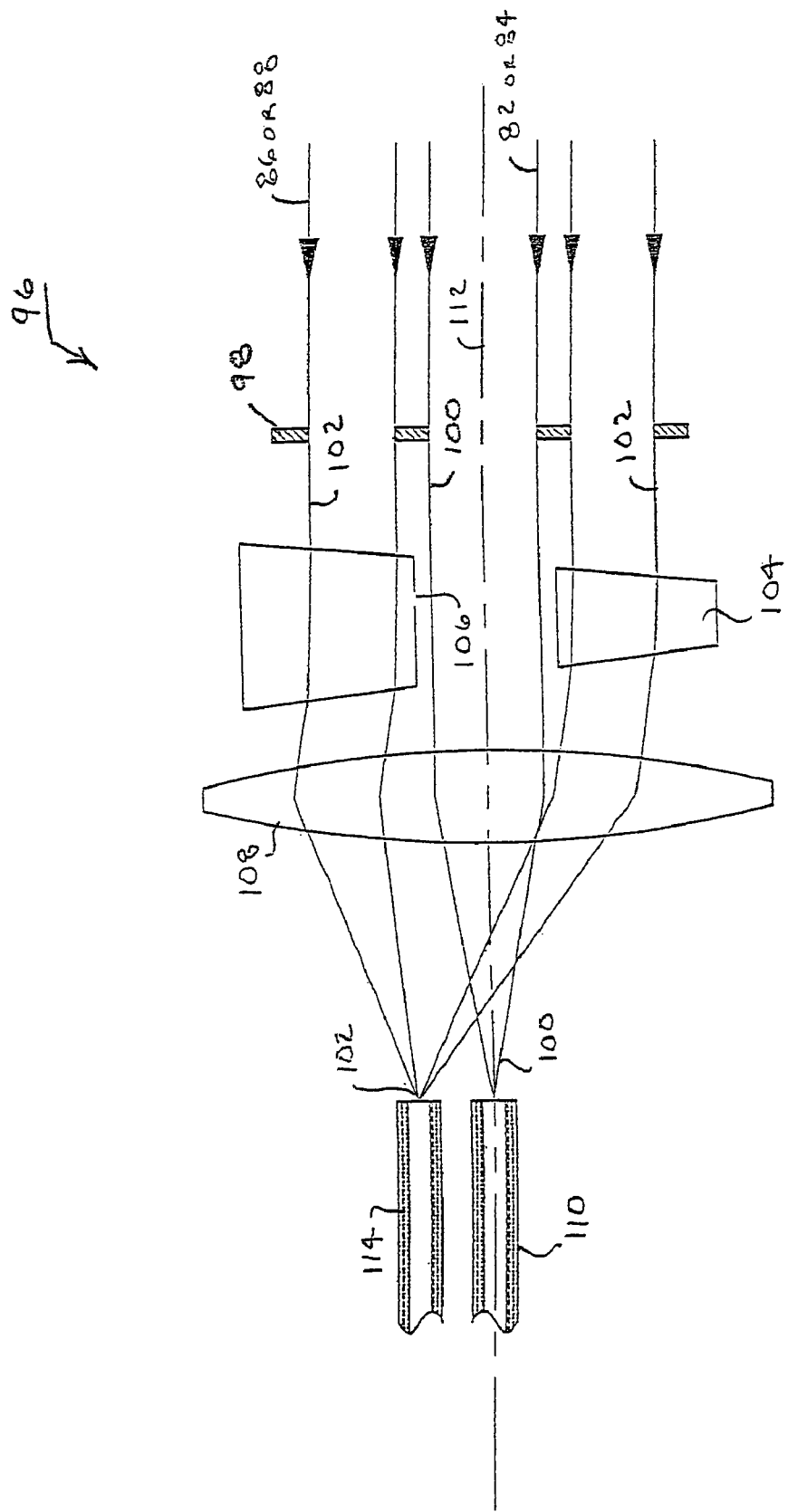
FIG. 7 is a diagram of a spatial separator within the data acquisition system for separating heterodyne signals associated with the test material-measuring beam portions from the instrument-measuring beam portions.

For example, FIG. 7 shows an exemplary spatial separator 96 for separating the heterodyne signal beams 82 and 86 or 84 and 88. An aperture mask 98 (a) separates an incoming beam into a central core portion 100 corresponding to the heterodyne signal beams 82 or 84 and an outer annulus portion 102 corresponding to the heterodyne signal beams 86 or 88 and (b) eliminates any areas of spatial overlap or ambiguity between the signal beams. A transparent wedge 104 with a hollow central aperture 106 produces an angular separation between the central core portion 100 and the outer annulus portion 102. The central core portion 100 transmits through the central aperture without change to a convex lens 108 that focuses the central core portion 100 incident upon an optical fiber 110 located along a common optical axis 112 of the wedge 104 and lens 108. The outer annulus portion 102 is refracted by the wedge 104 and is focused by the convex lens 108 incident upon an optical fiber 114 that is offset from the optical axis 112.

Figure 8:
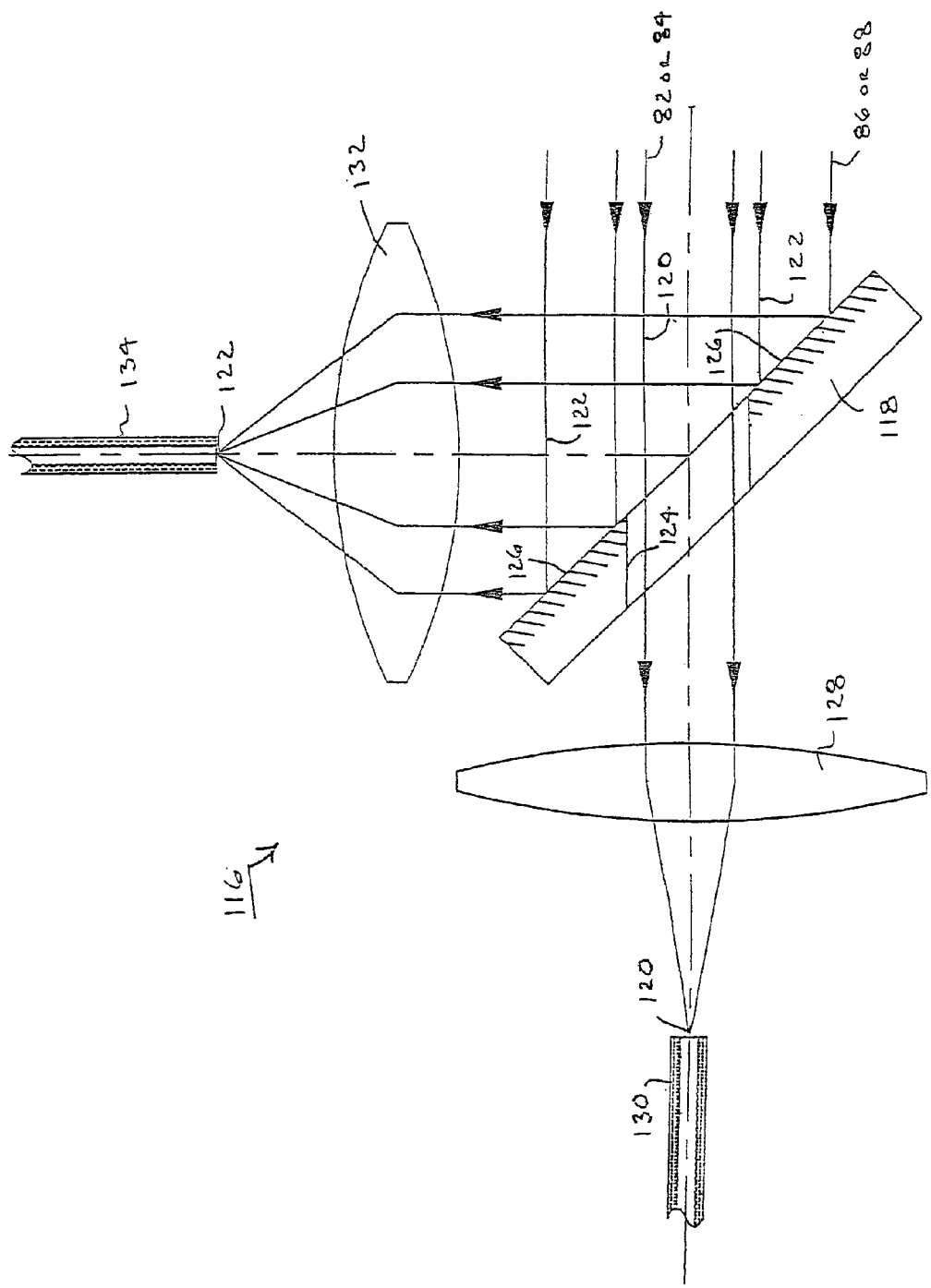
FIG. 8 is a diagram of an alternative spatial separator.

An alternative spatial separator 116 shown in FIG. 8 includes a beamsplitter 118 that functions as both an aperture mask and an angular separator for further distinguishing a central core portion 120 and an outer annulus portion 122 of the incoming signal composed of one or the other of the heterodyne signal beam pairings 82, 86 or 84, 88. The beamsplitter 118 includes distinct transmissive and reflective sections 124 and 126. The central core portion 120 transmits directly through the transmissive section 124, which is formed as a hole through the beamsplitter 118, to a convex lens 128 that focuses the central core portion 120 incident upon an optical fiber 130. The outer annulus portion 122 reflects from the reflective section 126 of the beamsplitter 118 to a convex lens 132 that focuses the outer annulus portion 122 incident upon an optical fiber 134.

The optical fibers 110, 114, or 130, 134 convey the individual heterodyne signal beams 82, 84, 86, and 88 to opto-electronic detectors that convert the heterodyne signal beams 82, 84, 86, and 88 into corresponding heterodyne electronic signals occupying four separate electronic channels. Alternatively, the spatial separators 96 and 116 could be arranged to focus the separated heterodyne signal beams 82, 84, 86, and 88 directly onto similar opto-electronic detectors. The data acquisition system 80 also includes processing capability for synchronously demodulating the four corresponding heterodyne electronic signals against a electronic reference signal at the common beat frequency. Phase variations of the corresponding heterodyne electronic signals from the electronic reference signal are interpreted as displacement-measuring signals relating to length variations of the test material 34 or the measurement loop 26.

The displacement-measuring signals are based on measurements of optical path length variations undergone by the test material-measuring portions 54 and 56 and the instrument-measuring portions 58 and 60 of the two-frequency test beam 18 as decoded from the heterodyne signal beams 82, 84, 86, and 88. A data processor 140 manipulates the displacement-measuring signals with each other for separating displacements of the measuring loop 26 from displacements of the test material 34 and makes associations with the temperature variation-measuring signal to produce a measurement of the displacement variation of the test material 34 as a function of its temperature variation.

Figure 9:
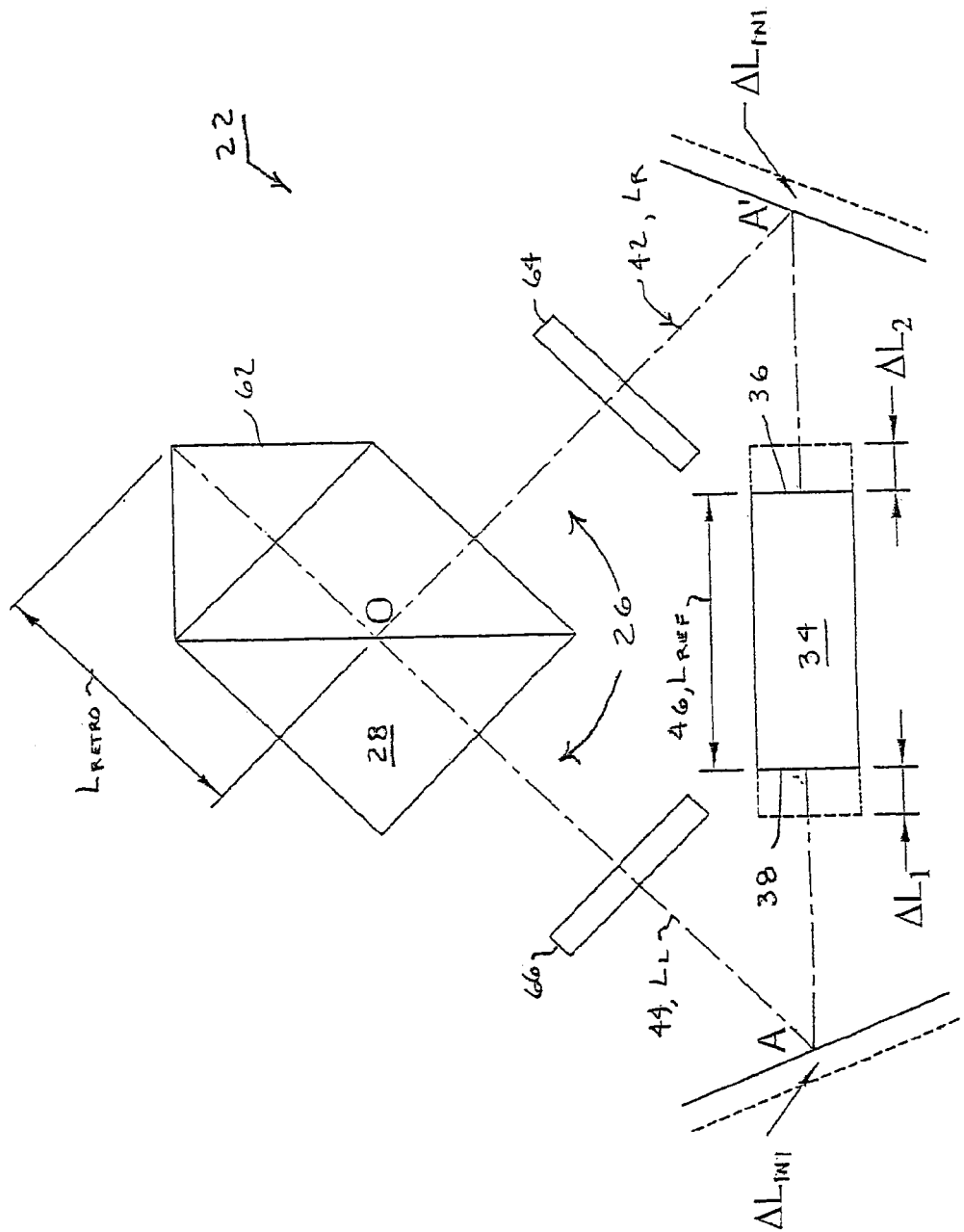
FIG. 9 is a layout of the test arm for referencing dimensions of the arm.

The preferred manipulations undertaken by the data processor 140 account for the contributions of each of the displacement measures extracted from the four heterodyne signal beams 82, 84, 86, and 88. With reference to FIG. 9, the first loop portion 42 of the measuring loop 26 that joins the test material end surface 36 to the test beam router 28 has an optical path length "$L_R$", the second loop portion 44 that joins the test material end surface 38 to the test beam router 28 has an optical path length of "$L_L$", and a third loop portion 46 that joins the first and second loop portions 42 and 44 between the two end surfaces 36 and 38 of the test material 34 has an optical path length of "$L_{REF}$". Also within the measuring loop 26 is an optical path length "$L_{RETRO}$" corresponding to the pathway between the test beam router 28 and the retroreflector 62.

Since the test material-measuring portion 54 of the test beam 18 reflects twice from the test material end surface 36 and once from the retroreflector 62, the total optical path length "$SPL_{1p}$" traversed by the test material-measuring portion 54 of the test beam 18 within the measuring loop 26 is given as:

$$SPL_{1p} = 4L_R + 2L_{RETRO} \quad (A1)$$

A change in optical path length "$\Delta SPL_{1p}$" undergone by the test material-measuring beam portion 54 is given by:

$$\Delta SPL_{1p} = \Delta 4L_R + \Delta 2L_{RETRO} \quad (A2)$$

Within this relationship, a change in the optical path length "$\Delta L_R$" is a combination of a change due to the test material 34 "$\Delta L_1$" and a change due to the instrument structure (i.e., measuring loop 26) "$\Delta L_{IN1}$" as follows:

$$\Delta L_R = \Delta L_1 + \Delta L_{IN1} \quad (A3)$$

By substitution, the change in optical path length "$\Delta SPL_{1p}$" undergone by the test material-measuring beam portion 54 can be rewritten as:

$$\Delta SPL_{1p} = 4(\Delta L_1 + \Delta L_{IN1}) + 2\Delta L_{RETRO} \quad (A4)$$

A similar expression can be written for the change in optical path length "$\Delta SPL_{2s}$" undergone by the test material-measuring beam portion 56 as follows:

$$\Delta SPL_{2s} = 4(\Delta L_2 + \Delta L_{IN2}) + 2\Delta L_{RETRO} \quad (A5)$$

The combined change in the optical path lengths traversed by the two test material-measuring beam portions 54 and 56 can be written as a combination of the path length changes undergone by the test material 34 and the changes undergone by the instrument structure (i.e., measuring loop 26) as follows:

$$\Delta SPL_{1p} + \Delta SPL_{2s} = 4(\Delta L_1 + \Delta L_2) + 4[\Delta L_{IN1} + \Delta L_{IN2} + \Delta L_{RETRO}] \quad (A6)$$

Within this expression is the expression for the actual change in dimension of the test material 34 as follows:

$$\Delta L = \Delta L_1 + \Delta L_2 \quad (A7)$$

However, extracting this information from the combined change in the optical path lengths traversed by the two test material-measuring beam portions 54 and 56 requires eliminating the contributions due to the spurious changes in the dimensions of the measuring loop. 26. The instrument-measuring portions 58 and 60 of the test beam 18 account for most of these spurious dimensional changes.

The total optical path length "$IPL_{1p}$" traversed by the instrument-measuring portion 58 of the test beam 18 within the measuring loop 26 is given as:

$$IPL_{1p} = 2[L_R + L_L + L_{REF} + L_{RETRO}] \quad (A8)$$

A change in optical path length "$\Delta IPL_{1p}$" undergone by the instrument-measuring beam portion 58 is given by:

$$\Delta IPL_{1p} = 2[\Delta L_R + \Delta L_L + \Delta L_{REF} + \Delta L_{RETRO}] \quad (A9)$$

Since the test material 34 is entirely bypassed, the change in the optical path lengths "$\Delta L_R$" and "$\Delta L_L$" are due entirely to the changes in the instrument structure "$\Delta L_{IN1}$" and "$\Delta L_{IN2}$" as follows:

$$\Delta L_R = \Delta L_{IN1} \quad (A10)$$

$$\Delta L_L = \Delta L_{IN2} \quad (A11)$$

Thus, expressions for the change in the optical path length "$\Delta IPL_{1p}$" undergone by the instrument-measuring beam portion 58 and a change in the optical path length "$\Delta IPL_{2s}$" undergone by the instrument-measuring beam portion 60 are given by:

$$\Delta IPL_{1p} = 2[\Delta L_{IN1} + \Delta L_{IN2} + \Delta L_{REF} + \Delta L_{RETRO}] \quad (A12)$$

$$\Delta IPL_{2s} = 2[\Delta L_{IN1} + \Delta L_{IN2} + \Delta L_{REF} + \Delta L_{RETRO}] \quad (A13)$$

The combined change in the optical path lengths traversed by the two instrument-measuring beam portions 58 and 60 can be written as:

$$\Delta IPL_{1p} + \Delta IPL_{2s} = 4[\Delta L_{IN1} + \Delta L_{IN2} + \Delta L_{RETRO}] + 4\Delta L_{REF} \quad (A14)$$

Subtracting the combined change in the optical path lengths traversed by the two instrument-measuring beam portions 58 and 60 from the combined change in the optical path lengths traversed by the two test material-measuring beam portions 54 and 56 yields the equality:

$$(\Delta SPL_{1p} + \Delta SPL_{2s}) - (\Delta IPL_{1p} + \Delta IPL_{2s}) = 4(\Delta L_1 + \Delta L_2) - 4\Delta L_{REF} \quad (A15)$$

Rewriting, it is apparent that the change "$\Delta L$" in the length of the test material 34 can be expressed in terms of the changes in the lengths of the two test material-measuring beam portions 54 and 56 and the two instrument-measuring beam portions 58 and 60 of the test beam 18 as:

$$\Delta L = \frac{1}{4}[(\Delta SPL_{1p} + \Delta SPL_{2s}) - (\Delta IPL_{1p} + \Delta IPL_{2s}) + 4\Delta L_{REF}] \quad (A16)$$

The final term "$\Delta L_{REF}$" is a residual source of uncertainty arising from the instrument-measuring beam portions 58 and 60 traversing the additional distance occupied by the test material 34. However, the contributions of this error source are expected to be small, especially if the measuring loop 26 including the third loop portion 46 is contained within an evacuated space.

Figure 10B:
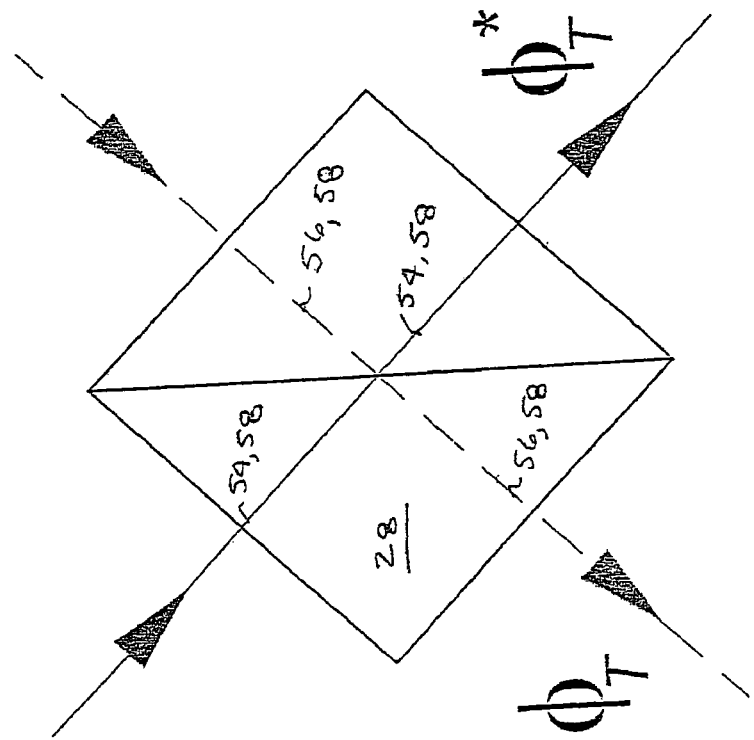
FIGS. 10A and 10B are layouts of the test beam router for referencing various interfaces of the router.
Figure 10A:
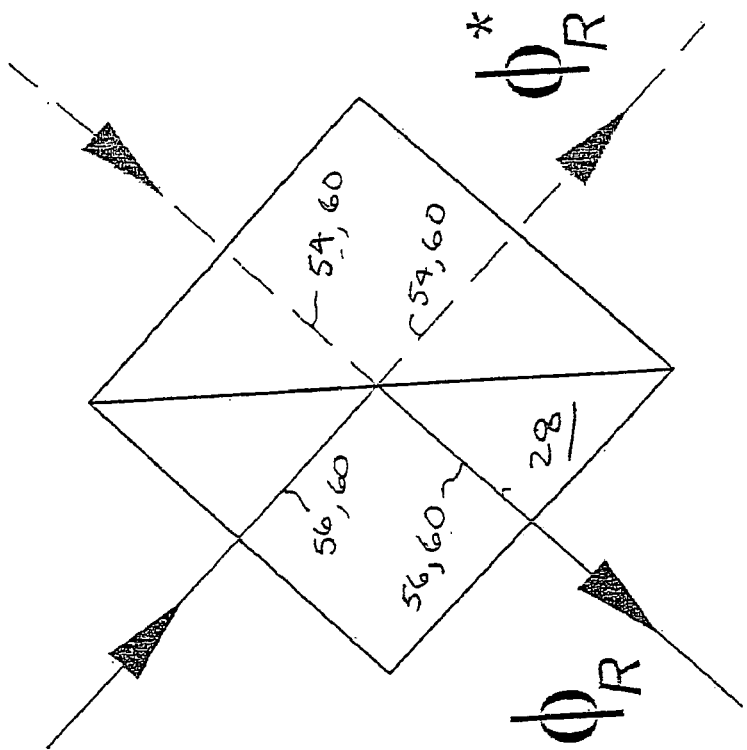

While the just-described model provides an overall explanation of the contributions of each measurement portion 54, 56, 58, and 60 decoded from the heterodyne signals 82, 84, 86, and 88, additional sources of error are apparent from changes in phase change accompanying reflections and transmissions at the various interfaces (see FIGS. 10A and 10B) of the measuring loop 26. The following table provides a list of changes in phase change at the various interfaces of the measuring loop 26.

Changes in phase change on reflection for various surfaces

| Symbol | Description |
| --- | --- |
| $\Delta\phi_R$ | Change in phase change on reflection at the test beam router between the main beam router and the second loop portion |
| $\Delta\phi_R^*$ | Change in phase change on reflection at the test beam router between the retroreflector and the first loop portion |
| $\Delta\phi_T$ | Change in phase change on transmission through the test beam router between the retroreflector and the second loop portion |
| $\Delta\phi_T^*$ | Change in phase change on transmission through the test beam router between the main beam router and the first loop portion |
| $\Delta\phi_V$ | Change in phase change on reflection at vertex mirror |
| $\Delta\phi_{TEST\ MATERIAL}$ | Change in phase change on reflection at test material end face |
| $\Delta\phi_{RETRO}$ | Change in phase change on reflection at retroreflector |

The effects of these changes in phase change "$\Delta\phi_{subscript}$" on the test material-measuring beam portions 54 and 56 can be included by modifying equations (A4) and (A5) to include the various changes in phase change "$\Delta\phi_{subscript}$", such that:

$$\Delta SPL_{1p} = 4(\Delta L_1 + \Delta L_{IN1} + \Delta\phi_V) + \quad (B1)$$
$$2(\Delta L_{RETRO} + \Delta\phi_T^* + \Delta\phi_R^* + \Delta\phi_{SAMPLE}) + \Delta\phi_{RETRO}$$

$$\Delta SPL_{2s} = 4(\Delta L_2 + \Delta L_{IN2} + \Delta\phi_V) + \quad (B2)$$
$$2(\Delta L_{RETRO} + \Delta\phi_T + \Delta\phi_R + \Delta\phi_{SAMPLE}) + \Delta\phi_{RETRO}$$

An expression combining the dimensional changes reflected in both test material-measuring beam portions 54 and 56 can be expressed in terms of the change in the length "$\Delta L$" of the test material 34, the errors due to the spurious changes in the measuring loop 26, and the errors due to changes in phase change "$\Delta\phi_{subscript}$" at the measuring loop interfaces as follows:

$$\Delta SPL_{1p} + \Delta SPL_{2s} = \quad (B3)$$
$$8\Delta\phi_V + 4(\Delta L_1 + \Delta L_2) + 4(\Delta L_{IN1} + \Delta L_{IN2} + \Delta L_{RETRO}) +$$
$$4\Delta\phi_{SAMPLE} + 2(\Delta\phi_T^* + \Delta\phi_R^* + \Delta\phi_T + \Delta\phi_R + \Delta\phi_{RETRO})$$

New expressions for the displacements measured by the instrument-measuring beam portions 58 and 60 and incorporating terms for changes in phase change "$\Delta\phi_{subscript}$" at the various interfaces are given by:

$$\Delta IPL_{1p} = 4\Delta\phi_V + \Delta\phi_{RETRO} + [ \quad (B4)$$
$$\Delta L_{IN1} + \Delta L_{IN2} + \Delta L_{REF} + \Delta L_{RETRO} + \Delta\phi_T^* + \Delta\phi_T]$$

$$\Delta IPL_{2s} = 4\Delta\phi_V + \Delta\phi_{RETRO} + \quad (B5)$$
$$2[\Delta L_{IN1} + \Delta L_{IN2} + \Delta L_{REF} + \Delta L_{RETRO} + \Delta\phi_R^* + \Delta\phi_R]$$

The sum of the above two expressions as seen below is a measure of the spurious changes in the measuring loop 26. The two expressions are not exactly equal due to the slight difference in path between the two instrument-measuring beam portions 58 and 60. This difference in path enables the expression combining the dimensional changes in both instrument-measuring beam portions 58 and 60 to account for corresponding path differences between the test material-measuring beam portions 54 and 56.

$$\Delta IPL_{1p} + \Delta IPL_{2s} = \quad (B6)$$
$$+8\Delta\phi_V + 4\Delta L_{REF} + 4(\Delta L_{IN1} + \Delta L_{IN2} + \Delta L_{RETRO}) +$$
$$2(\Delta\phi_T^* + \Delta\phi_T + \Delta\phi_R^* + \Delta\phi_R + \Delta\phi_{RETRO})$$

As expressed below, subtracting the sum of the displacements measured by the instrument-measuring beam portions 58 and 60 from the sum of the displacements measured by the test material-measuring beam portions 54 and 56 has the effect of canceling all the spurious influences of the interface changes in phase change "$\Delta\phi_{subscript}$" except for the changes in phase change "$\Delta\phi_{test\ material}$" associated with reflections from the test material end surfaces 36 and 38.

$$(\Delta SPL_{1p} + \Delta SPL_{2s}) - (\Delta IPL_{1p} + \Delta IPL_{2s}) = \quad (B7)$$
$$4(\Delta L_1 + \Delta L_2) + 4\Delta\phi_{sample} - 4\Delta L_{REF}$$

Rewriting the above expression for the change "$\Delta L$" in the length of the test material 34 now yields an additional term for the measured displacement as follows:

$$\Delta L = \quad (B8)$$
$$\frac{1}{4}[(\Delta SPL_{1p} + \Delta SPL_{2s}) - (\Delta IPL_{1p} + \Delta IPL_{2s}) + 4\Delta L_{REF} - 4\Delta\phi_{sample}]$$

This additional term arises from the changes in phase change "$\Delta\phi_{test\ material}$" on reflection at the test material end surfaces 36 and 38 with temperature. While the sum of the measured changes in phase change from the combined instrument-measuring beam portions 58 and 60 contains sufficient information to allow cancellation of uncertainty contributions due to changes in phase change "$\Delta\phi_{subscript}$" on reflection and transmission at all the other interfaces of the measuring loop 26, no information is available from the instrument-measuring beam portions 58 and 60 about the changes in phase change "$\Delta\phi_{test\ material}$" that occur upon reflection from the test material end surfaces 36 and 38.

The changes in phase change "$\Delta\phi_{test\ material}$" with temperature accompanying reflections from the test material end surfaces 36 and 38 are regarded as systematic errors that can be estimated by taking additional measurements. One such estimation technique is based on the method described in a paper by M. Okaji, N. Yamada, K. Nara, and H. Kato entitled "Laser interferometric device at low temperatures: application to fused silica SRM 739," *Cryogenics* 35, pp. 887-891, 1995, which is hereby incorporated by reference. This method requires an instrument such as our device 10 that accommodates the measurement of test materials of various lengths. The method is described below.

Consider a measurement made in the presence of systematic errors, "$\Delta L_{systematic}$". Let the measured and actual change in dimension be "$\Delta L_{Measured}$" and "$\Delta L_{Actual}$" respectively. The measured change in dimension is then given by:

$$\Delta L_{Measured} = \Delta L_{Actual} + \Delta L_{Systematic} \tag{C1}$$

The systematic error can be cancelled by measuring specimens of different lengths, provided the systematic error is repeatable from one measurement to another. Let "$\Delta L_{Measured,j}$" where "j=1,2" represents the measured change in dimension for two test materials of length "$L_j$". Similarly, let "$\Delta L_{Actual,j}$" represent the actual or desired change in dimension. Then $$\Delta L_{Measured,1} = \Delta L_{Actual,1} + \Delta L_{Systematic} \tag{C2}$$

$$\Delta L_{Measured,2} = \Delta L_{Actual,2} + \Delta L_{Systematic} \tag{C3}$$

Assuming the systematic error to be the same and also assuming that the CTE of the two specimens is the same, the systematic error can be eliminated by subtracting one measurement from the other, i.e., $$\Delta L_{Measured,1} - \Delta L_{Measured,2} = \Delta L_{Actual,1} - \Delta L_{Actual,2} \tag{C4}$$

The right-hand side of the above equation represents the net length change of a specimen of length "$L_1-L_2$". This method of error estimation is only possible in an instrument that permits the measurement of test materials of different lengths with minimal changes to the rest of the instrument. This method relies on the fact that the absolute change in dimension of the test material scales with the test material length.

Figure 11:
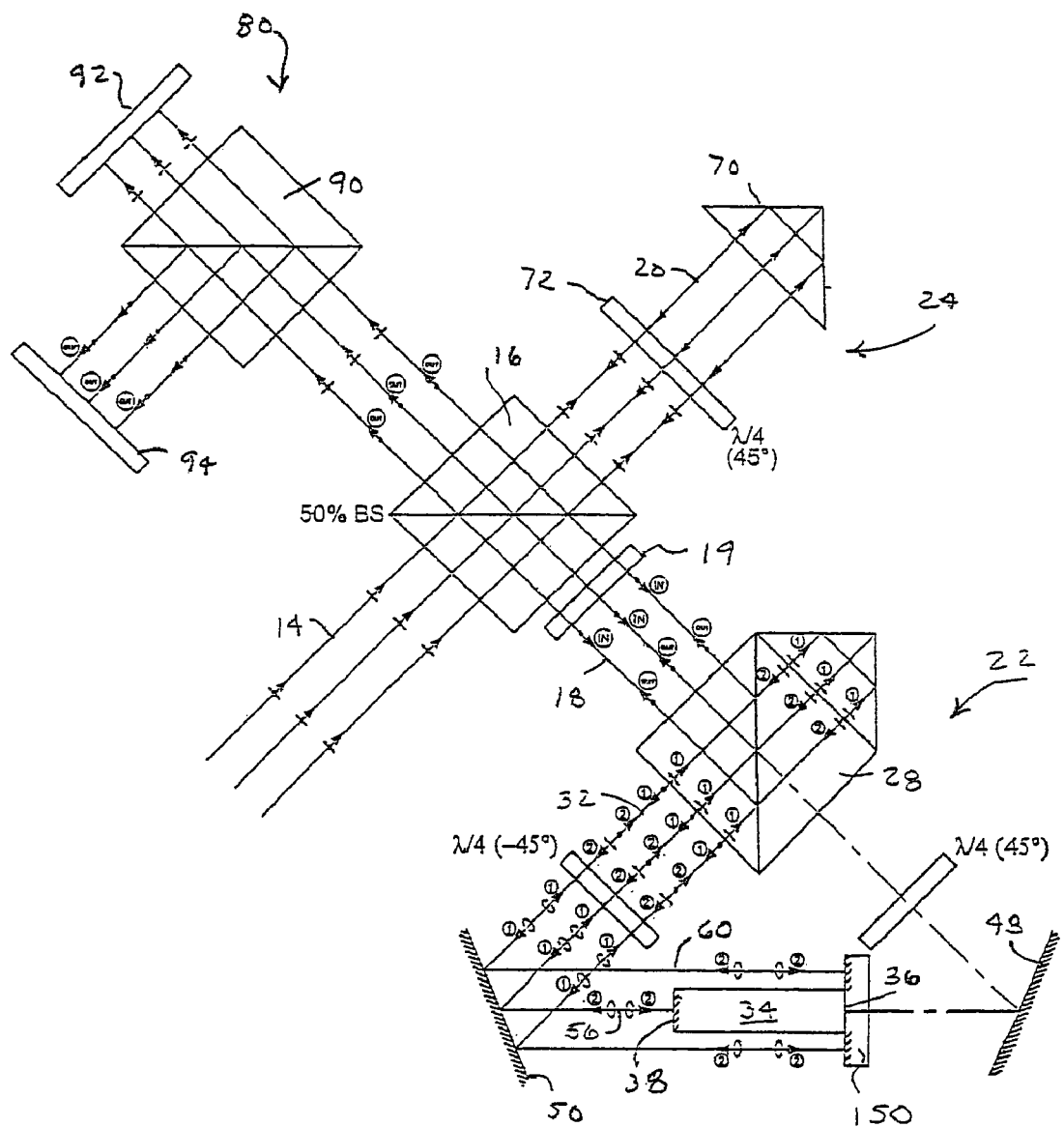
FIG. 11 is an alternative measuring configuration for making single-sided measurements with an auxiliary optic.

The primary measurement configuration for our device 10 is shown in FIGS. 1-3 for performing double-pass measurements within the test arm 22 against both end surfaces 36 and 38 of the test material 34. However, our interferometer 10 can be readily adapted to carry out alternative measuring protocols for purposes of comparison. Such alternative protocols include:

Single-sided measurement with an auxiliary optic attached to one end of the test material
Double-sided measurement with a finite thickness reference artifact
Double-sided measurement with a "zero" thickness reference artifact
Double-sided measurement with the test material being a spacer in a Fabry-Perot cavity FIG. 11 illustrates a single-sided measurement with an auxiliary optic 150. One measurement is made directly from the end surface 38 of the test material 34, while a second indirect measurement of the other test material end surface 36 made using the auxiliary optic 150 that is optically contacted to the test material. Only one of the test material-measuring beam portions, the portion 56, and one of the instrument-measuring beam portions, the portion 60, are used. The test material-measuring beam portion 56 reflects from the test material end surface 38, and the instrument-measuring beam portion 60 reflects from the auxiliary optic 150, which is attached to the test material 34 and serves as the reference. Only the second-frequency test beam 32 having an "s" polarization is required to reach the test arm 22; the other, the first-frequency test beam 30, having a "p" polarization is blocked by a polarizer 19 in advance of the test arm 22. Just two of the four measurement channels are used in this configuration.

Figure 12:
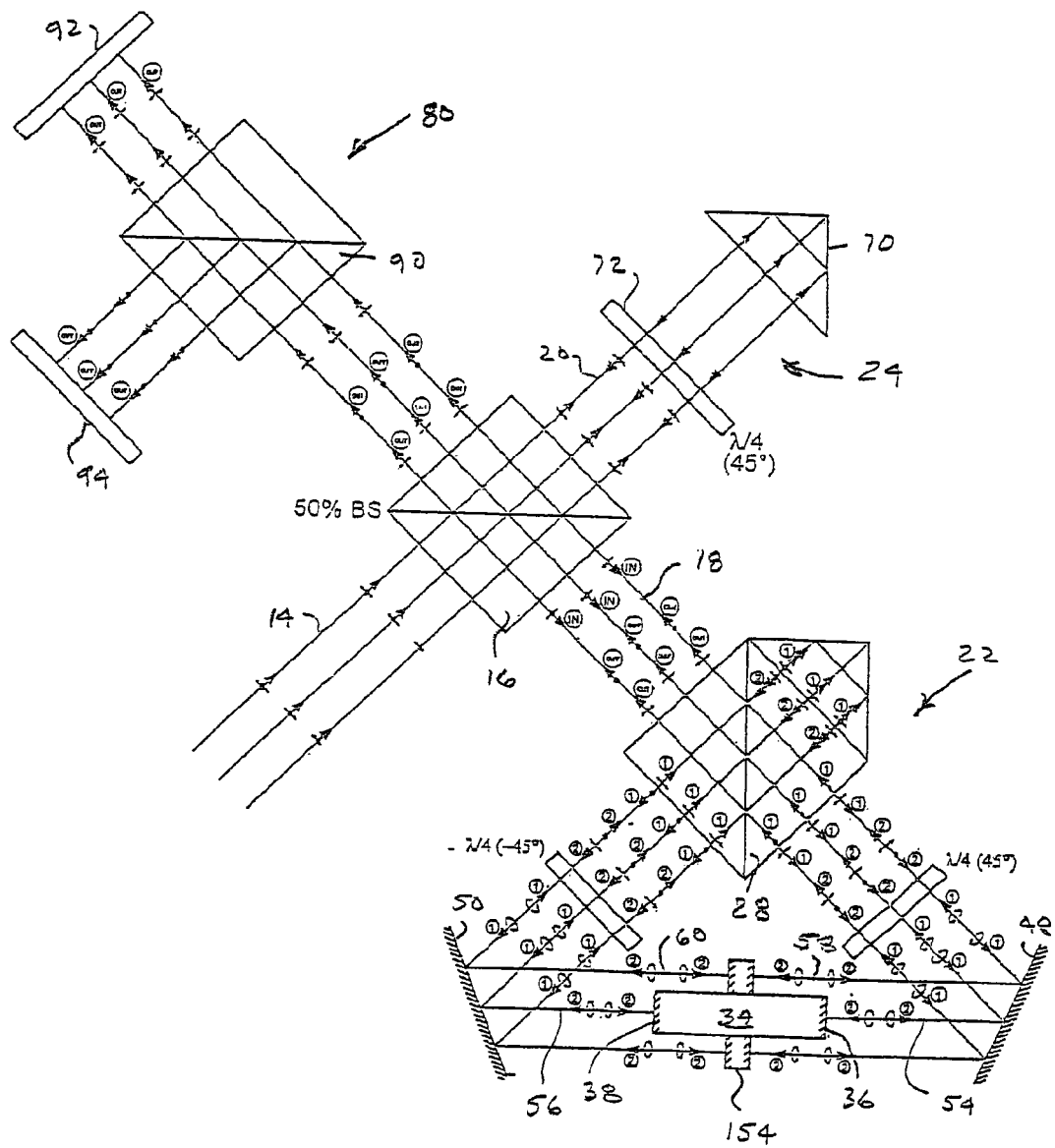
FIG. 12 is an alternative measuring configuration for making double-sided measurements with a finite thickness reference artifact.

FIG. 12 illustrates a double-sided measurement with a finite thickness reference artifact 154. This measurement configuration incorporates two separate Michelson interferometers. The test material-measuring beam portions 54 and 56, which are used as test beams, reflect from the two test material end surfaces 36 and 38; and the instrument-measuring beam portions 58 and 60, which are used as reference beams, reflect from a thin test material of a low-expansion material identified as the reference artifact 154. Since thermal expansion is proportional to the absolute dimension of the artifact 154, the uncertainty contribution due to thin reference artifact 154 is limited. Assuming the same coating behavior, the changes in phase change on reflection from the coatings on the reference artifact 154 and from the coatings on the test material end surfaces 36 and 38 are "common mode" in this configuration. All four of the output channels are used to perform the measurement.

Figure 13:
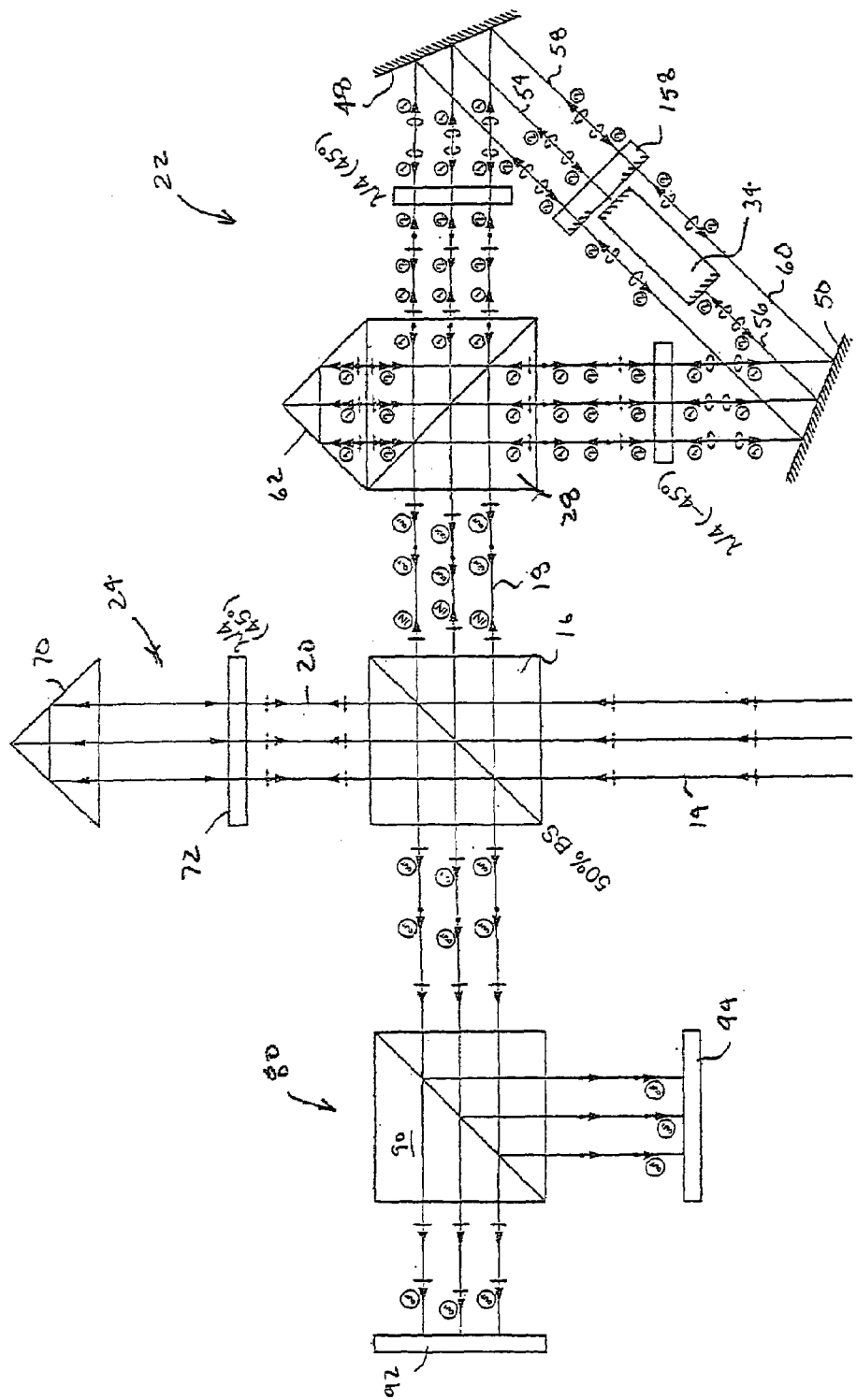
FIG. 13 is an alternative measuring configuration for making double-sided measurements with a "zero" thickness reference artifact.

A similar configuration is shown in FIG. 13 for a double-sided measurement with a so-called "zero" thickness reference artifact 158, which is considered as the limiting case of the previous configuration. Reducing the effective thickness of the reference artifact 158 to near zero reduces the uncertainty contribution of the reference artifact 158 even further. This is achieved by forming the reference artifact 158 from a transparent material that is partially coated on one side so as to provide a central clear aperture for the test material-measuring beam portion 54 to reach the test material end surface 36 and to provide a reflective outer annulus that reflects both instrument-measuring beam portions 58 and 60. The artifact 158 is positioned to the right of the test material 34 in FIG. 13, but can be located on either side. This measurement utilizes all four of the output channels to perform the measurement.

Figure 14:
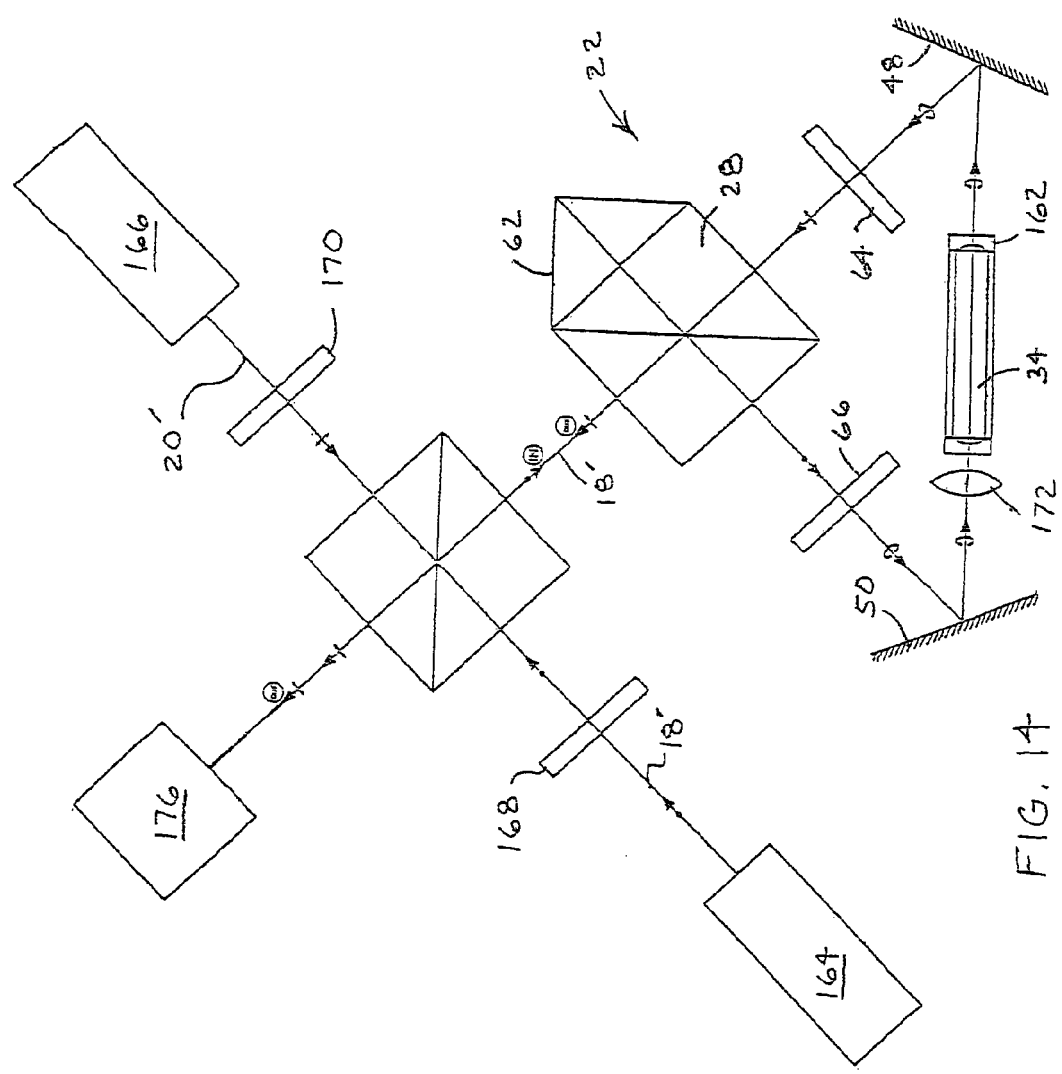
FIG. 14 is an alternative measuring configuration for making systematic measurements with a measurement test material as a spacer in a Fabry-Perot cavity.

FIG. 14 depicts a double-sided measurement with the test material 34 mounted as a spacer in a high-finesse confocal Fabry-Perot cavity 162. The Fabry-Perot cavity 162 is formed by optically contacting mirrors with high-reflectance coatings to the end of the test material 34. The test material 34 has optically flat and parallel end faces and a hole cored along its axis. Expansion of the cavity is measured by probing the cavity with a laser and measuring the change in the resonance frequency of the cavity. A narrow collimated test beam 18' is fed into the test arm 22 instead of the collimated broad beam used in the other configurations. The narrowed test beam 22 has a single polarization state, which determines the direction of propagation through the cavity 162.

A tunable laser 164 and a frequency stabilized laser 166 are used. The tunable laser 164 produces the test beam 18', which encounters a polarizer 168 before reaching the main beam router 16. The frequency stabilized laser 166 produces a reference beam 20', which encounters a similar polarizer 170 en route to the main beam router 16. The two polarizers 168 and 170 are rotated by 90 degrees to block cross effects between the lasers 164 and 166. Upon entering the test arm 22, the test beam 18' is reflected at test beam router 28 and is directed into the cavity 162 after reflection from the vertex mirror 50 and passage through mode-matching optics 172. Both quarter-wave retarders 64 and 66 are oriented at 45°, with the result that the polarization state of emerging test beam 18' is orthogonal to the incoming state of the test beam. As such, the emerging test beam 18' transmits through the test beam router 28 and exits the test arm 22. Alternately, the two quarter-wave retarders 64 and 66 could be replaced by a single half-wave plate oriented at 45° and located at the exit of the cavity 162. The rotated polarization state of the emerging test beam 18' also allows transmission through the main beam router 16. The reference beam 20' having a matching polarization state is combined with the emerging test beam 18' at the main beam router 16. The beat frequency that is observed at a detector 176 is a measure of the difference in frequency between the two lasers. The change in the beat frequency is a measure of the change in dimension of the cavity 162.

The original configuration of our device 10 provides for a high-accuracy for the measurement of the CTE (coefficient of thermal expansion) of ultra-low expansion materials. Accuracies of less than one part per billion per degree centigrade are contemplated in contrast to prior devices, our new device can detect changes in dimension of the entire measuring loop 26 for distinguishing the contributions of the test material 34 and the machine structure to measured displacements.

Although auxiliary optics can be added to perform alternative measuring protocols, the preferred configuration of our system eliminates the use of auxiliary optics and procedures such as optical contacting that produce errors. The system also facilitates the measurement of systematic errors that can remain in the measurement, such as changes in phase change with temperature associated with the test material end surfaces 36 and 38. The systematic errors can be determined by making measurements on test materials of different lengths, which can be readily accommodated by the design.

Although the invention is described with respect to a dilatometer configuration arranged for the measurement of thermal expansion/contraction characteristics of ultra-low thermal expansion materials, the invention can be similarly configured for measuring dimensional changes induced by a variety of internal or external influences beyond temperature, such as exposure to variations in pressure, humidity, and other environmental effects.

We claim:

1. Device for high-accuracy measurement of dimensional changes in a test material comprising: a source for producing a measuring beam; a main beam router that divides the measuring beam into test and reference beams; a measuring loop that includes an optical pathway to the test material; a test beam router that directs both a test material-measuring portion of the test beam and an instrument-measuring portion of the test beam along a common path of the measuring loop that includes the optical pathway to the test material; the main beam router providing for recombining the test material-measuring portion of the test beam with a first portion of the reference beam and for recombining the instrument-measuring portion of the test beam with a second portion of the reference beam; a data acquisition system that converts optical path length differences between the recombined test and reference beams into processable displacement measurements relating to length variations of both the test material and the measuring loop; and a data processor that manipulates the displacement measurements to separate length variations of the measuring loop from length variations of the test material to produce a more accurate measure of the length variation of the test material.

2. The device of claim 1 in which the test material-measuring portion of the test beam acquires information concerning the length variations of the test material in combination with the length variations of the measuring loop, and the instrument-measuring portion of the test beam acquires information concerning the length variations of the measuring loop independently of the length variations of the test material.

3. The device of claim 1 in which the measuring loop includes: a first loop portion that joins a first surface of the test material to the test beam router, a second loop portion that joins a second surface of the test material to the test beam router, and a third loop portion that joins the first and second loop portions between the first and second surfaces of the test material.

4. The device of claim 3 in which the first loop portion is arranged for conveying a first test material-measuring portion of the test beam in opposite directions between the test beam router and a first surface of the test material, and the second loop portion is arranged for conveying a second test material-measuring portion of the test beam in opposite directions between the test beam router and a second surface of the test material.

5. The device of claim 4 in which the first, second, and third loop portions are arranged for conveying the instrument-measuring portion of the test beam along the measuring loop beginning and ending at the test beam router.

6. The device of claim 1 in which the source is a multi-frequency laser source that produces a beam of light having two primary frequencies and the main beam router divides the two-frequency beam of light into a two-frequency test beam and a two-frequency reference beam.

7. The device of claim 6 in which the test beam router divides the two-frequency test beam into a first-frequency test beam and a second-frequency test beam.

8. The device of claim 7 in which the measuring loop includes: a first loop portion that conveys a test material-measuring portion of the first-frequency test beam in opposite directions between the test beam router and a first surface of the test material, a second loop portion that conveys a test material-measuring portion of the second-frequency test beam in opposite directions between the test beam router and a second surface of the test material, and a third loop portion that together with the first and second loop portions conveys instrument-measuring portions of the first- and second-frequency test beams in opposite directions along the measuring loop beginning and ending at the test beam router.

9. The device of claim 8 further comprising a reference arm that returns first-and second-frequency portions of the two-frequency reference beam to the main router.

10. The device of claim 9 in which the main beam router recombines the two-frequency test and reference beams.

11. The device of claim 10 in which the data acquisition system separates the combined beams into four heterodyne signals as follows: the test material-measuring portion of the first-frequency test beam is combined with a first portion of the second-frequency reference beam to form a first heterodyne signal, the test material-measuring portion of the second-frequency test beam is combined with a first portion of the first-frequency reference beam to form a second heterodyne signal, the instrument-measuring portion of the first-frequency test beam is combined with a second portion of the second-frequency reference beam to form a third heterodyne signal, and the instrument-measuring portion of the second-frequency test beam is combined with a second portion of the first-frequency reference beam to form a fourth heterodyne signal.

12. The device of claim 11 in which the data acquisition system converts the four heterodyne signals into displacement-measuring signals.

13. The device of claim 7 in which the two frequencies emitted by the multi-frequency laser source are linearly polarized in different orthogonal directions and the test beam router is a polarizing beamsplitter that exploits the different linear polarizations to separate the two-frequency test beam into the first-frequency test beam and the second-frequency test beam.

14. The device of claim 13 in which the main beam router recombines the first-frequency portions of the test beam with corresponding second-frequency portions of the reference beam, and recombines the second-frequency portions of the test beam with corresponding first-frequency portions of the reference beam.

15. The device of claim 14 in which a retarder relatively rotates polarizations between the two-frequency test beam and the two-frequency reference beam.

16. The device of claim 1 further comprising a retroreflector associated with the test beam router that doubles path lengths of the test material-measuring portions of the test beam twice reflecting from the surfaces of the test material.

17. The device of claim 16 in which the retroreflector inverts the test material-measuring portions of the test beam between reflections from the surfaces of the test material.

18. The device of claim 1 in which the measuring loop has a triangular configuration with the test beam router located at an apex and two directional mirrors located at base vertices.

19. The device of claim 18 in which a mounting for the test material is located between the directional mirrors.

20. The device of claim 1 arranged as a dilatometer for measuring a thermal expansion/contraction characteristic of the test material and further comprising a temperature modifying system that produces a temperature variation in the test material along with a measurement of the temperature variation.

21. The device of claim 20 in which the data acquisition system associates the manipulated displacement measurements with the measurement of temperature variation to produce the measure of the length variation of the test material in relation to the temperature variation of the test material.

22. A device for measuring dimensional changes of a test material comprising: a multi-frequency laser source that produces a beam of light having two primary frequencies; a main beam router that divides the two-frequency beam of light into a two-frequency test beam and a two-frequency reference beam; a measuring loop including: a test beam router that divides the two-frequency test beam into a first-frequency test beam and a second-frequency test beam, a first loop portion that joins a first surface of the test material to the test beam router, a second loop portion that joins a second surface of the test material to the test beam router, and a third loop portion that joins the first and second loop portions between the first and second surfaces of the test material; the first loop portion being arranged for conveying a test material-measuring portion of the first-frequency test beam in opposite directions between the test beam router and a first surface of the test material; the second loop portion being arranged for conveying a test material-measuring portion of the second-frequency test beam in opposite directions between the test beam router and a second surface of the test material; the third loop portion together with the first and second loop portions being arranged for conveying instrument-measuring portions of the first- and second-frequency test beams in opposite directions along the measuring loop beginning and ending at the test beam router; the main beam router also being arranged for recombining portions of the two-frequency test and reference beams for forming: a first heterodyne test material signal combining the test material-measuring portion of the first-frequency test beam and a portion of the second-frequency reference beam, a second heterodyne test material signal combining the test material-measuring portion of the second-frequency test beam and a portion of the first-frequency reference beam, a third heterodyne instrument signal combining the instrument-measuring portion of the first-frequency test beam and a portion of the second-frequency reference beam, and a fourth heterodyne instrument signal combining the instrument-measuring portion of the second-frequency test beam and a portion of the first-frequency reference beam; a data acquisition system that acquires the first, second, third, and fourth heterodyne signals for producing corresponding displacement-measuring signals; and a data processor that manipulates the displacement-measuring signals with each other for separating displacements of the measuring loop from displacements of the test material to produce a measure of the displacement variation of the test material.

23. The device of claim 22 in which the two frequencies emitted by the multi-frequency laser source are linearly polarized in different orthogonal directions and the test beam router is a polarizing beamsplitter that exploits the different linear polarizations to separate the two-frequency test beam into the first-frequency test beam and the second-frequency test beam.

24. The device of claim 23 in which a retarder relatively rotates polarizations between the two-frequency test beam and the two-frequency reference beam.

25. The device of claim 24 in which the main beam router recombines the first-frequency portions of the test beam with the corresponding second-frequency portions of the reference beam having a common polarization, and recombines the second-frequency portions of the test beam with corresponding first-frequency portions of the reference beam having an orthogonal common polarization.

26. The device of claim 25 further comprising a retroreflector associated with the polarizing beamsplitter for doubling path lengths of the test material-measuring portions of the test beam by twice reflecting the test material-measuring portions of the test beam from the surfaces of the test material.

27. The device of claim 26 in which the retroreflector also provides for doubling path lengths of the instrument-measuring portions of the test beam, each traversing the measurement loop twice in opposite directions.

28. The device of claim 27 in which the retroreflector inverts the test material-measuring portions of the test beam between reflections from the surfaces of the test material and inverts the instrument-measuring portions of the test beam between the opposite directions of traverse around the measuring loop.

29. The device of claim 22 in which the measuring loop has a triangular configuration with the test beam router located at an apex and two directional mirrors located at base vertices.

30. The device of claim 29 in which a mounting for the test material is located between the directional mirrors.

31. The device of claim 22 in which the first-and second-frequency test beams each occupy larger transverse areas than the end surfaces of the test material and are divided by transverse regions into the test material-measuring and instrument-measuring portions.

32. The device of claim 31 in which the first-and second-frequency test beams are sized larger in diameter than the surfaces of the test material, allowing the instrument-measuring portions of the test beams to propagate around the test material.

33. The device of claim 31 in which the test material is formed with a hollow portion that allows the instrument-measuring portions of the test beams to propagate through the test material.

34. The device of claim 22 arranged for measuring thermal expansion/contraction characteristics of the test material and further comprising a temperature modifying system that: varies the temperature of the test material, measures the variation in temperature of the test material, and produces a temperature-variation measuring signal corresponding to the temperature variation of the test material.

35. The device of claim 34 in which the data processor makes associations with the temperature variation-measuring signal to produce the measure of the displacement variation of the test material in relation to the temperature variation of the test material.

36. A device for measuring dimensional changes of a test material comprising: a source for producing a measuring beam; a measuring loop that includes an optical pathway to the test material; a beam router within the measuring loop for directing the measuring beam in opposite directions; directional optics within the measuring loop for directing opposite directions of the measuring beam toward opposite surfaces of the test material; the measuring beam being formed with a larger transverse area than a transverse area of the test material surfaces for dividing the measuring beam into a test material-measuring portion and an instrument-measuring portion; and a data processor that manipulates the displacement measurements of the test material-measuring and instrument-measuring portions of the measuring beam to separate length variations of the measuring loop from length variations of the test material to produce a measure of the length variation of the test material.

37. The device of claim 36 in which the measuring loop has a triangular configuration with the test beam router located at an apex and the two directional optics located at base vertices.

38. The device of claim 36 in which the beam router directs both the test material-measuring portion of the measuring beam and the instrument-measuring portion of the measuring beam along a common path of the measuring loop that includes the optical pathway to the test material.

39. The device of claim 36 in which the measuring loop includes: a first loop portion that joins a first surface of the test material to the beam router, a second loop portion that joins a second surface of the test material to the beam router, and a third loop portion that joins the first and second loop portions between the first and second surfaces of the test material.

40. The device of claim 39 in which: the first loop portion is arranged for conveying a first test material-measuring portion of the measuring beam in opposite directions between the beam router and a first surface of the test material, the second loop portion being arranged for conveying a second test material-measuring portion of the measuring beam in opposite directions between the beam router and a second surface of the test material, and the third loop portion together with the first and second loop portions being arranged for conveying instrument-measuring portions of the measuring beam in opposite directions along the measuring loop beginning and ending at the beam router.

41. The device of claim 36 in which the source is a multi-frequency laser source that produces a beam of light having two primary frequencies.

42. The device of claim 41 in which the beam router is one of a plurality of beam routers including a main beam router that divides the two-frequency beam of light into a two-frequency test beam and a two-frequency reference beam.

43. The device of claim 42 in which the beam router is one of a plurality of beam routers including a test beam router within the measuring loop that divides the two-frequency test beam into a first-frequency test beam and a second-frequency test beam.

44. The device of claim 43 in which the test beam router within the measuring loop directs the first-and second-frequency test beams in opposite directions for engaging the opposite surfaces of the test material.

45. The device of claim 44 in which the main beam router recombines portions of the two-frequency test and reference beams for forming: a first heterodyne test material signal combining a test material-measuring portion of the first-frequency test beam and a portion of the second-frequency reference beam, a second heterodyne test material signal combining a test material-measuring portion of the second-frequency test beam and a portion of the first-frequency reference beam, a third heterodyne instrument signal combining an instrument-measuring portion of the first-frequency test beam and a portion of the second-frequency reference beam, and a fourth heterodyne instrument signal combining an instrument-measuring portion of the second-frequency test beam and a portion of the first-frequency reference beam.

46. The device of claim 36 arranged for measuring a thermal expansion/contraction characteristic of the test material and further comprising a temperature modifying system that produces a temperature variation in the test material along with a measurement of the temperature variation.

47. The device of claim 46 in which the data processor associates the manipulated displacement measurements with the measurement of temperature variation to produce the measure of the length variation of the test material in relation to the temperature variation of the test material.

* * * * *